United States Patent
Ortiz et al.

(10) Patent No.: US 11,076,890 B2
(45) Date of Patent: Aug. 3, 2021

(54) ROD-TO-ROD CONNECTORS HAVING ROBUST ROD CLOSURE MECHANISMS AND RELATED METHODS

(71) Applicant: Medos International SARL, Le Locle (CH)

(72) Inventors: Aubrey Ortiz, Boston, MA (US); Kevin Lee, Canton, MA (US); Frank Spratt, Middleboro, MA (US); Robert Carruth, North Attleboro, MA (US); Samuel Jacobs, Acton, MA (US); Mark Hall, Bridgewater, MA (US)

(73) Assignee: Medos International Sàrl, Le Locle (CH)

( * ) Notice: Subject to any disclaimer, the term of this patent is extended or adjusted under 35 U.S.C. 154(b) by 84 days.

(21) Appl. No.: 15/828,805

(22) Filed: Dec. 1, 2017

(65) Prior Publication Data
US 2019/0167313 A1    Jun. 6, 2019

(51) Int. Cl.
*A61B 17/70* (2006.01)
(52) U.S. Cl.
CPC ...... *A61B 17/7049* (2013.01); *A61B 17/7083* (2013.01); *A61B 17/7019* (2013.01)
(58) Field of Classification Search
CPC .............. A61B 17/7049; A61B 17/705; A61B 17/7052; A61B 17/7043; A61B 17/7047; A61B 17/7056; A61B 17/7083
See application file for complete search history.

(56) References Cited

U.S. PATENT DOCUMENTS 5,261,909 A    11/1993    Sutterlin et al.
5,312,405 A    5/1994    Korotko et al.
(Continued)

FOREIGN PATENT DOCUMENTS

CN    201194833 Y    2/2009
EP    1857064 A1    11/2007
(Continued)

OTHER PUBLICATIONS

[No Author Listed] VuePoint II Technique Guide, 2015, NuVasive®, Inc.; 64 pages.
(Continued)

*Primary Examiner* — Eduardo C Robert
*Assistant Examiner* — Christina NegrelliRodriguez
(74) *Attorney, Agent, or Firm* — Barnes & Thornburg LLP

(57) ABSTRACT

Various rod-to-rod connectors having robust rod closure mechanisms and related methods are disclosed herein, e.g., for enhancing the locking or clamping force on a rod. An exemplary connector can provide a robust closure mechanism for rod-to-rod connections in which the run-on length of a rod slot is minimal. The connector can include a moveable jaw that is partially disposed within a connector body and configured to pivot or translate relative to the connector body to form a fully or substantially closed rod slot around a first rod. The closed rod slot can be formed between a first rod-receiving recess defined in the connector body and a counterpart first rod-receiving recess defined in the moveable jaw. The locking or clamping force of the moveable jaw can be amplified by a mechanical advantage caused by the force exerted to lock a second rod in a second rod-receiving slot of the connector body.

44 Claims, 18 Drawing Sheets

(56) References Cited

U.S. PATENT DOCUMENTS

| | | |
|---|---|---|
| 5,569,246 A | 10/1996 | Ojima et al. |
| 5,613,968 A | 3/1997 | Lin |
| 5,667,506 A | 9/1997 | Sutterlin |
| 5,709,685 A | 1/1998 | Dombrowski et al. |
| 5,716,355 A | 2/1998 | Jackson et al. |
| 5,725,528 A | 3/1998 | Errico |
| 5,769,857 A | 6/1998 | Reztzov et al. |
| 5,776,135 A | 7/1998 | Errico et al. |
| 5,876,403 A | 3/1999 | Shitoto |
| 5,885,284 A | 3/1999 | Errico et al. |
| 5,980,523 A | 11/1999 | Jackson |
| 6,050,997 A | 4/2000 | Mullane |
| 6,083,226 A | 7/2000 | Fiz |
| 6,096,039 A | 8/2000 | Stoltenberg et al. |
| 6,231,575 B1 | 5/2001 | Krag |
| 6,238,396 B1 | 5/2001 | Lombardo |
| 6,248,104 B1 | 6/2001 | Chopin et al. |
| 6,280,443 B1 | 8/2001 | Gu et al. |
| 6,309,390 B1 | 10/2001 | Le Couedic et al. |
| 6,328,739 B1 | 12/2001 | Liu et al. |
| 6,328,740 B1 | 12/2001 | Richelsoph |
| 6,402,751 B1 | 6/2002 | Hoeck et al. |
| 6,468,276 B1 | 10/2002 | McKay |
| 6,478,798 B1 | 11/2002 | Howland |
| 6,524,310 B1 | 2/2003 | Lombardo et al. |
| 6,551,318 B1 | 4/2003 | Stahurski |
| 6,554,832 B2 | 4/2003 | Shluzas |
| 6,592,585 B2 | 7/2003 | Lee et al. |
| 6,616,668 B2 | 9/2003 | Altarec et al. |
| 6,676,661 B1 | 1/2004 | Martin Benlloch et al. |
| 6,736,775 B2 | 5/2004 | Phillips |
| 6,736,820 B2 | 5/2004 | Biedermann et al. |
| 6,783,526 B1 | 8/2004 | Lin et al. |
| 6,786,907 B2 | 9/2004 | Lange |
| 6,793,657 B2 | 9/2004 | Lee et al. |
| 6,974,460 B2 | 12/2005 | Carbone et al. |
| 7,029,474 B2 | 4/2006 | Richelsoph et al. |
| 7,104,993 B2 | 9/2006 | Baynham et al. |
| 7,122,036 B2 | 10/2006 | Vanacker |
| 7,163,538 B2 | 1/2007 | Altarac et al. |
| 7,166,108 B2 | 1/2007 | Mazda et al. |
| 7,179,261 B2 | 2/2007 | Sicvol et al. |
| 7,189,236 B2 | 3/2007 | Taylor et al. |
| 7,485,132 B1 | 2/2009 | McBride et al. |
| 7,572,277 B2 | 8/2009 | Roussouly et al. |
| 7,575,587 B2 | 8/2009 | Rezach et al. |
| 7,585,314 B2 | 9/2009 | Taylor et al. |
| 7,628,799 B2 | 12/2009 | Richelsoph et al. |
| 7,666,210 B2 | 2/2010 | Franck et al. |
| 7,704,270 B2 | 4/2010 | De Coninck |
| 7,717,938 B2 | 5/2010 | Kim et al. |
| 7,717,940 B2 | 5/2010 | Woods et al. |
| 7,744,632 B2 | 6/2010 | Usher |
| 7,744,634 B2 | 6/2010 | Farris |
| 7,753,940 B2 | 7/2010 | Veldman et al. |
| 7,771,474 B2 | 8/2010 | Cordaro |
| 7,789,897 B2 | 9/2010 | Sanders |
| 7,794,478 B2 | 9/2010 | Nilsson |
| 7,803,174 B2 | 9/2010 | Denis et al. |
| 7,806,912 B2 | 10/2010 | Lawton et al. |
| 7,833,248 B2 | 11/2010 | Markworth et al. |
| 7,837,714 B2 | 11/2010 | Drewry et al. |
| 7,842,071 B2 | 11/2010 | Hawkes |
| 7,901,434 B2 | 3/2011 | Drewry et al. |
| 7,909,854 B2 | 3/2011 | Schwab |
| 7,922,746 B2 | 4/2011 | Miller |
| 7,922,747 B2 | 4/2011 | Kirschman |
| 7,927,355 B2 | 4/2011 | Berrevoets et al. |
| 7,942,901 B2 | 5/2011 | Rezach |
| 7,947,066 B2 | 5/2011 | Tepper et al. |
| 7,959,653 B2 | 6/2011 | Thramann et al. |
| 7,993,371 B2 | 8/2011 | Farris |
| 8,016,862 B2 | 9/2011 | Felix et al. |
| 8,025,679 B2 | 9/2011 | Nichols et al. |
| 8,062,338 B2 | 11/2011 | McBride et al. |
| 8,075,594 B2 | 12/2011 | Purcell |
| 8,080,037 B2 | 12/2011 | Butler et al. |
| 8,097,022 B2 | 1/2012 | Marik |
| 8,109,974 B2 | 2/2012 | Boomer et al. |
| 8,114,133 B2 | 2/2012 | Logan |
| 8,147,519 B2 | 4/2012 | Wilcox |
| 8,152,851 B2 | 4/2012 | Mueller et al. |
| 8,167,908 B2 | 5/2012 | Ely et al. |
| 8,172,879 B2 | 5/2012 | Butler et al. |
| 8,192,467 B2 | 6/2012 | Felix et al. |
| 8,197,515 B2 | 6/2012 | Levy et al. |
| 8,236,028 B2 | 8/2012 | Kalfas et al. |
| 8,241,334 B2 | 8/2012 | Butler et al. |
| 8,246,657 B1 | 8/2012 | Samuel |
| 8,246,665 B2 | 8/2012 | Butler et al. |
| 8,262,700 B2 | 9/2012 | Cho et al. |
| 8,262,701 B2 | 9/2012 | Rathbun et al. |
| 8,292,924 B2 | 10/2012 | Neary et al. |
| 8,298,266 B2 | 10/2012 | Miller |
| 8,298,269 B2 | 10/2012 | Null et al. |
| 8,317,837 B2 | 11/2012 | Rezach et al. |
| 8,337,527 B2 | 12/2012 | Hawkins et al. |
| 8,337,532 B1 | 12/2012 | McLean et al. |
| 8,366,749 B2 | 2/2013 | Sweeney |
| 8,366,750 B2 | 2/2013 | Iott et al. |
| 8,414,616 B2 | 4/2013 | Berrevoets et al. |
| 8,414,617 B2 | 4/2013 | Young et al. |
| 8,419,771 B2 | 4/2013 | Poirier et al. |
| 8,419,773 B2 | 4/2013 | Biedermann et al. |
| 8,430,916 B1 | 4/2013 | Winslow et al. |
| 8,460,342 B2 | 6/2013 | Courtney et al. |
| 8,470,001 B2 | 6/2013 | Trautwein et al. |
| 8,591,550 B2 | 11/2013 | Ludwig et al. |
| 8,617,213 B2 | 12/2013 | Moore et al. |
| 8,628,559 B2 | 1/2014 | Iott et al. |
| 8,641,739 B2 | 2/2014 | McLean et al. |
| 8,657,856 B2 | 2/2014 | Gephart et al. |
| 8,668,721 B2 | 3/2014 | Miller |
| 8,715,323 B2 | 5/2014 | Ballard et al. |
| 8,721,689 B2 | 5/2014 | Butler et al. |
| 8,728,124 B2 | 5/2014 | Miller |
| 8,758,411 B1 | 6/2014 | Rayon et al. |
| 8,771,319 B2 | 7/2014 | Prajapati |
| 8,808,332 B2 | 8/2014 | Iott et al. |
| 8,828,056 B2 | 9/2014 | Buss et al. |
| 8,864,798 B2 | 10/2014 | Weiman et al. |
| 8,864,799 B2 | 10/2014 | Kraus |
| 8,870,923 B2 | 10/2014 | Richelsoph |
| 8,882,803 B2 | 11/2014 | Iott et al. |
| 8,888,777 B2 | 11/2014 | Mullaney |
| 8,888,819 B2 | 11/2014 | Frasier et al. |
| 8,920,471 B2 | 12/2014 | Barrus et al. |
| 8,920,475 B1 | 12/2014 | Ziemek et al. |
| 8,945,186 B2 | 2/2015 | Walker et al. |
| 8,951,289 B2 | 2/2015 | Matityahu |
| 8,998,956 B2 | 4/2015 | George et al. |
| 8,998,961 B1 | 4/2015 | Ziemek et al. |
| 9,005,249 B2 | 4/2015 | Rinner et al. |
| 9,023,087 B2 | 5/2015 | Frankel et al. |
| 9,055,980 B2 | 6/2015 | Biedermann |
| 9,060,815 B1 | 6/2015 | Gustine et al. |
| 9,072,547 B2 | 7/2015 | Harper et al. |
| 9,084,630 B2 | 7/2015 | Mullaney |
| 9,095,380 B2 | 8/2015 | Mir et al. |
| 9,101,400 B2 | 8/2015 | Trieu et al. |
| 9,101,405 B2 | 8/2015 | Dickinson et al. |
| 9,107,703 B2 | 8/2015 | Torres |
| 9,113,961 B2 | 8/2015 | Larroque-Lahitette |
| 9,119,675 B2 | 9/2015 | Lee et al. |
| 9,125,691 B2 | 9/2015 | Gunn |
| 9,131,963 B2 | 9/2015 | Predick |
| 9,131,964 B2 | 9/2015 | Blain et al. |
| 9,149,301 B2 | 10/2015 | Asaad et al. |
| 9,155,565 B2 | 10/2015 | Boomer et al. |
| 9,155,580 B2 | 10/2015 | Cormier et al. |
| 9,186,184 B2 | 11/2015 | Janowski |
| 9,198,696 B1 | 12/2015 | Bannigan et al. |
| 9,204,901 B2 | 12/2015 | Black et al. |
| 9,220,541 B1 | 12/2015 | Dant et al. |

(56) References Cited

U.S. PATENT DOCUMENTS

| | | | |
|---|---|---|---|
| 9,247,964 B1 | 2/2016 | Shoshtaev |
| 9,265,548 B2 | 2/2016 | Jones et al. |
| 9,271,763 B2 | 3/2016 | Barrus et al. |
| 9,339,307 B2 | 5/2016 | McClintock et al. |
| 9,345,521 B2 | 5/2016 | Ziolo |
| 9,421,041 B2 | 8/2016 | Richelsoph |
| 9,433,445 B2 | 9/2016 | Ramsay et al. |
| 9,451,994 B1 | 9/2016 | Whipple et al. |
| 9,474,554 B2 | 10/2016 | Strnad |
| 9,517,089 B1 | 12/2016 | Casey et al. |
| 9,561,058 B2 | 2/2017 | Lange et al. |
| 9,579,126 B2 | 2/2017 | Zhang et al. |
| 9,615,867 B2 | 4/2017 | Picetti et al. |
| 9,629,663 B2 | 4/2017 | Ludwig et al. |
| 9,649,136 B2 | 5/2017 | George et al. |
| 9,693,808 B2 | 7/2017 | Fauth et al. |
| 9,724,131 B2 | 8/2017 | Bootwala et al. |
| 9,770,269 B1 | 9/2017 | Shoshtaev |
| 9,956,009 B1 | 5/2018 | Shoshtaev |
| 10,238,432 B2 | 3/2019 | Carruth et al. |
| 10,321,939 B2 | 6/2019 | Lee et al. |
| 10,398,476 B2 | 9/2019 | Lee et al. |
| 10,492,835 B2 | 12/2019 | Lee et al. |
| 10,517,647 B2 | 12/2019 | Lee et al. |
| 10,561,454 B2 | 2/2020 | Lee et al. |
| 2002/0042614 A1 | 4/2002 | Ueyama et al. |
| 2003/0045878 A1 | 3/2003 | Petit et al. |
| 2003/0045879 A1 | 3/2003 | Minfelde et al. |
| 2003/0153914 A1 | 8/2003 | Oribe et al. |
| 2004/0111088 A1 | 6/2004 | Picetti et al. |
| 2004/0147929 A1 | 7/2004 | Biedermann et al. |
| 2004/0162558 A1 | 8/2004 | Hegde et al. |
| 2005/0131404 A1 | 6/2005 | Mazda et al. |
| 2005/0171537 A1 | 8/2005 | Mazel et al. |
| 2005/0228326 A1 | 10/2005 | Kalfas et al. |
| 2005/0228377 A1 | 10/2005 | Chao et al. |
| 2005/0228378 A1 | 10/2005 | Kalfas et al. |
| 2005/0228382 A1 | 10/2005 | Richelsoph et al. |
| 2006/0039750 A1 | 2/2006 | Thomke et al. |
| 2006/0058789 A1* | 3/2006 | Kim .................. A61B 17/7049 606/914 |
| 2006/0064090 A1 | 3/2006 | Park |
| 2006/0064091 A1 | 3/2006 | Ludwig et al. |
| 2006/0079892 A1 | 4/2006 | Roychowdhury et al. |
| 2006/0177263 A1 | 8/2006 | Thomke et al. |
| 2006/0206114 A1 | 9/2006 | Ensign et al. |
| 2006/0229611 A1 | 10/2006 | Avery et al. |
| 2006/0241598 A1 | 10/2006 | Khalili |
| 2006/0282074 A1 | 12/2006 | Renaud et al. |
| 2007/0049932 A1* | 3/2007 | Richelsoph .......... A61B 17/645 606/252 |
| 2007/0100339 A1 | 5/2007 | Clement et al. |
| 2007/0123860 A1 | 5/2007 | Francis et al. |
| 2007/0173825 A1 | 7/2007 | Sharifi-Mehr et al. |
| 2007/0173829 A1 | 7/2007 | Drewry et al. |
| 2007/0233062 A1 | 10/2007 | Berry |
| 2007/0233090 A1 | 10/2007 | Naifeh et al. |
| 2007/0250061 A1 | 10/2007 | Chin et al. |
| 2007/0270805 A1 | 11/2007 | Miller et al. |
| 2007/0270817 A1 | 11/2007 | Rezach |
| 2007/0270818 A1 | 11/2007 | Rezach |
| 2007/0276384 A1* | 11/2007 | Spratt ................ A61B 17/7056 606/276 |
| 2008/0021466 A1 | 1/2008 | Shadduck et al. |
| 2008/0045963 A1 | 2/2008 | Abdou |
| 2008/0058805 A1 | 3/2008 | Stuart |
| 2008/0082112 A1 | 4/2008 | Lawton et al. |
| 2008/0109039 A1 | 5/2008 | Michielli et al. |
| 2008/0177318 A1 | 7/2008 | Veldman et al. |
| 2008/0177323 A1 | 7/2008 | Null et al. |
| 2008/0234743 A1 | 9/2008 | Marik |
| 2008/0255617 A1 | 10/2008 | Cho et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0281361 A1 | 11/2008 | Vittur et al. |
| 2009/0036929 A1 | 2/2009 | Reglos et al. |
| 2009/0082812 A1 | 3/2009 | Lewis |
| 2009/0105765 A1 | 4/2009 | Strnad |
| 2009/0157120 A1 | 6/2009 | Marino et al. |
| 2009/0163956 A1 | 6/2009 | Biedermann et al. |
| 2009/0187217 A1 | 7/2009 | Weiman et al. |
| 2009/0204153 A1 | 8/2009 | Suzuki et al. |
| 2009/0222042 A1 | 9/2009 | Firkins et al. |
| 2009/0228046 A1 | 9/2009 | Garamszegi |
| 2009/0249851 A1 | 10/2009 | Isaacs |
| 2010/0004686 A1 | 1/2010 | Lemoine |
| 2010/0004693 A1 | 1/2010 | Miller et al. |
| 2010/0010545 A1 | 1/2010 | Park et al. |
| 2010/0087864 A1 | 4/2010 | Klein et al. |
| 2010/0087867 A1 | 4/2010 | Klein et al. |
| 2010/0094345 A1 | 4/2010 | Saidha et al. |
| 2010/0094346 A1 | 4/2010 | Matityahu |
| 2010/0094349 A1 | 4/2010 | Hammer et al. |
| 2010/0114165 A1 | 5/2010 | Ely |
| 2010/0114167 A1 | 5/2010 | Wilcox et al. |
| 2010/0160981 A1 | 6/2010 | Butler et al. |
| 2010/0204733 A1 | 8/2010 | Rathbun et al. |
| 2010/0241171 A1 | 9/2010 | Clement et al. |
| 2010/0274286 A1 | 10/2010 | Blain et al. |
| 2010/0280552 A1 | 11/2010 | Lee |
| 2010/0298884 A1 | 11/2010 | Faizan et al. |
| 2010/0324599 A1 | 12/2010 | Montello et al. |
| 2011/0034957 A1 | 2/2011 | Biedermann |
| 2011/0046675 A1 | 2/2011 | Barrus et al. |
| 2011/0066187 A1 | 3/2011 | Fang et al. |
| 2011/0087287 A1 | 4/2011 | Reeder, Jr. et al. |
| 2011/0087288 A1 | 4/2011 | Stevenson et al. |
| 2011/0098748 A1 | 4/2011 | Jangra |
| 2011/0106178 A1 | 5/2011 | Schwab |
| 2011/0112533 A1 | 5/2011 | Venturini et al. |
| 2011/0112580 A1 | 5/2011 | Clement et al. |
| 2011/0137345 A1 | 6/2011 | Stoll et al. |
| 2011/0152936 A1 | 6/2011 | Gil et al. |
| 2011/0196425 A1 | 8/2011 | Rezach et al. |
| 2011/0245872 A1 | 10/2011 | Nilsson |
| 2011/0245878 A1 | 10/2011 | Franks et al. |
| 2011/0307018 A1 | 12/2011 | Zucherman et al. |
| 2012/0029571 A1 | 2/2012 | Schwab et al. |
| 2012/0059421 A1 | 3/2012 | Aferzon |
| 2012/0071926 A1 | 3/2012 | Jani et al. |
| 2012/0083845 A1 | 4/2012 | Winslow et al. |
| 2012/0095512 A1 | 4/2012 | Nihalani |
| 2012/0130436 A1 | 5/2012 | Haskins et al. |
| 2012/0158064 A1 | 6/2012 | Kroll |
| 2012/0203278 A1 | 8/2012 | Gil et al. |
| 2012/0221053 A1 | 8/2012 | Copf |
| 2012/0226316 A1 | 9/2012 | Dant et al. |
| 2012/0232593 A1 | 9/2012 | Predick |
| 2012/0259369 A1 | 10/2012 | Hammer |
| 2012/0290013 A1 | 11/2012 | Simonson |
| 2012/0296335 A1 | 11/2012 | Mullaney |
| 2012/0303062 A1 | 11/2012 | Amstutz et al. |
| 2013/0018422 A1 | 1/2013 | Rinner et al. |
| 2013/0030468 A1 | 1/2013 | Le Couedic et al. |
| 2013/0079826 A1 | 3/2013 | Simonson |
| 2013/0085534 A1 | 4/2013 | Hainard et al. |
| 2013/0096617 A1 | 4/2013 | Ballard et al. |
| 2013/0123854 A1 | 5/2013 | Kondrashov et al. |
| 2013/0211457 A1 | 8/2013 | Dickinson et al. |
| 2013/0253588 A1 | 9/2013 | Traynelis et al. |
| 2013/0268004 A1 | 10/2013 | Rathbun |
| 2013/0274807 A1 | 10/2013 | Prajapati |
| 2013/0274808 A1 | 10/2013 | Larroque-Lahitette et al. |
| 2014/0018858 A1 | 1/2014 | Laeng et al. |
| 2014/0066990 A1 | 3/2014 | Akbarnia et al. |
| 2014/0088650 A1 | 3/2014 | Taddia et al. |
| 2014/0114359 A1 | 4/2014 | Hawkes |
| 2014/0135839 A1 | 5/2014 | Frankel et al. |
| 2014/0148856 A1 | 5/2014 | Ibarra et al. |
| 2014/0222076 A1 | 8/2014 | Jackson |
| 2014/0249581 A1 | 9/2014 | Stachniak |
| 2014/0277146 A1 | 9/2014 | Li et al. |
| 2014/0277160 A1 | 9/2014 | Ziolo |

(56) References Cited

U.S. PATENT DOCUMENTS

| | | |
|---|---|---|
| 2014/0277163 A1 | 9/2014 | Kretzer et al. |
| 2014/0303674 A1 | 10/2014 | Sasing |
| 2014/0316468 A1 | 10/2014 | Keiser et al. |
| 2014/0336706 A1 | 11/2014 | Garamszegi |
| 2014/0343613 A1 | 11/2014 | Eliasen et al. |
| 2015/0032160 A1 | 1/2015 | Carbone et al. |
| 2015/0057707 A1 | 2/2015 | Barrus et al. |
| 2015/0057708 A1 | 2/2015 | Ballard et al. |
| 2015/0073479 A1 | 3/2015 | Rinner |
| 2015/0094769 A1 | 4/2015 | Abbasi |
| 2015/0119941 A1 | 4/2015 | Daniels et al. |
| 2015/0190178 A1 | 7/2015 | McCarthy et al. |
| 2015/0196328 A1 | 7/2015 | Hirschl et al. |
| 2015/0223844 A1 | 8/2015 | Leff et al. |
| 2015/0230830 A1 | 8/2015 | Frankel et al. |
| 2015/0282842 A1 | 10/2015 | Beyar et al. |
| 2015/0313645 A1 | 11/2015 | Hansell |
| 2015/0359568 A1 | 12/2015 | Rezach |
| 2016/0135846 A1 | 5/2016 | Mirda |
| 2016/0143665 A1 | 5/2016 | Biedermann et al. |
| 2016/0166289 A1 | 6/2016 | Alsup et al. |
| 2016/0287294 A1 | 10/2016 | Kubo et al. |
| 2017/0020578 A1 | 1/2017 | Mosnier et al. |
| 2017/0079690 A1 | 3/2017 | Oberlander et al. |
| 2017/0086885 A1 | 3/2017 | Duncan et al. |
| 2017/0086895 A1 | 3/2017 | Barra et al. |
| 2017/0095271 A1 | 4/2017 | Faulhaber |
| 2017/0105764 A1 | 4/2017 | Williams |
| 2017/0112540 A1 | 4/2017 | Montello et al. |
| 2017/0119439 A1 | 5/2017 | Ozdil et al. |
| 2017/0128105 A1 | 5/2017 | Patrinicola et al. |
| 2017/0128107 A1 | 5/2017 | Alsup et al. |
| 2017/0209182 A1 | 7/2017 | Picetti et al. |
| 2017/0245900 A1 | 8/2017 | Rezach |
| 2017/0281247 A1 | 10/2017 | Murray et al. |
| 2017/0311985 A1 | 11/2017 | Bobbitt et al. |
| 2017/0333087 A1 | 11/2017 | Lee et al. |
| 2017/0333088 A1 | 11/2017 | Lee et al. |
| 2017/0348026 A1 | 12/2017 | Stein et al. |
| 2018/0042647 A1 | 2/2018 | Cowan et al. |
| 2018/0098798 A1 | 4/2018 | Italiaie et al. |
| 2018/0116695 A1 | 5/2018 | Armstrong et al. |
| 2018/0161073 A1 | 6/2018 | Lee et al. |
| 2018/0168694 A1 | 6/2018 | Lee et al. |
| 2018/0195150 A1 | 7/2018 | Meyer et al. |
| 2018/0206890 A1 | 7/2018 | Rezach |
| 2018/0228516 A1 | 8/2018 | Armstrong et al. |
| 2018/0228518 A1 | 8/2018 | Carruth et al. |
| 2018/0243009 A1 | 8/2018 | Bobbitt et al. |
| 2018/0280062 A1 | 10/2018 | Lee et al. |
| 2018/0280063 A1 | 10/2018 | Lee et al. |
| 2018/0317972 A1 | 11/2018 | Abbasi |
| 2019/0175226 A1 | 6/2019 | Carruth et al. |
| 2019/0183541 A1 | 6/2019 | Lee et al. |
| 2019/0269440 A1 | 9/2019 | Patrinicola et al. |
| 2019/0336178 A1 | 11/2019 | Finn et al. |
| 2019/0365432 A1 | 12/2019 | Lee et al. |
| 2020/0060729 A1 | 2/2020 | Lee et al. |
| 2020/0069341 A1 | 3/2020 | Abbasi |
| 2020/0085473 A1 | 3/2020 | Lee et al. |
| 2020/0170695 A1 | 6/2020 | Lee et al. |

FOREIGN PATENT DOCUMENTS

| | | |
|---|---|---|
| EP | 2 319 436 A1 | 5/2011 |
| EP | 2730242 A1 | 5/2014 |
| KR | 20100054713 A | 5/2010 |
| WO | 2005/044119 A2 | 5/2005 |
| WO | 2007124242 A1 | 11/2007 |
| WO | 2009/110865 A8 | 12/2009 |
| WO | 2011/004222 A1 | 1/2011 |
| WO | 2011/006155 A1 | 1/2011 |
| WO | 2015/017250 A1 | 2/2015 |

OTHER PUBLICATIONS

Akbarnia, B., et al., "Pediatric Isola® Prebent Rod Placement," (Technique Manual), DePuy Acromed, Oct. 2010; 2 pages.

International Search Report and Written Opinion for Application No. PCT/US2017/031883, dated Aug. 2, 2017. (15 pgs).

Invitation to Pay Additional Fees for Application No. PCT/US2018/017034, dated May 18, 2018 (18 pages).

International Search Report and Written Opinion for Application No. PCT/US2018/024731, dated Jul. 2, 2018 (17 pages).

U.S. Appl. No. 16/280,918, filed Feb. 20, 2019, Tandem Rod Connectors and Related Methods.

U.S. Appl. No. 16/443,849, filed Jun. 17, 2019, Implant Connectors and Related Methods.

International Search Report and Written Opinion for Application No. PCT/US2018/062786, dated Feb. 4, 2019 (15 pages).

U.S. Appl. No. 16/688,578, filed Nov. 19, 2019, Implant Connectors and Related Methods.

U.S. Appl. No. 16/782,030, filed Feb. 4, 2020, Articulating Implant Connectors and Related Methods.

International Search Report and Written Opinion for Application No. PCT/US2018/017034, dated Aug. 1, 2018 (20 pages).

U.S. Appl. No. 16/666,887, filed Oct. 29, 2019, Offset Rods, Offset Rod Connectors, and Related Methods.

U.S. Appl. No. 16/951,585, filed Nov. 18, 2020, Tandem Rod Connectors and Related Methods.

\* cited by examiner

ROD-TO-ROD CONNECTORS HAVING ROBUST ROD CLOSURE MECHANISMS AND RELATED METHODS

FIELD

Implant connectors and related methods are disclosed herein, including rod-to-rod connectors having robust rod closure mechanisms and related methods.

BACKGROUND

Fixation systems can be used in orthopedic surgery or neurosurgery to maintain a desired spatial relationship between multiple bones or bone fragments. For example, various conditions of the spine, such as fractures, deformities, and degenerative disorders, can be treated by attaching a spinal fixation system to one or more vertebrae. Such systems may include a spinal fixation element, such as a rod, that is coupled to the vertebrae by one or more bone anchors, such as screws or hooks. The fixation system can also include various other implants, such as rod-to-rod connectors for attaching multiple rods to one another. Once installed, the fixation system holds the vertebrae in a desired position until healing or spinal fusion can occur, or for some other period of time.

There are many instances in which it may be desirable to connect multiple implants to each other. For example, some revision surgeries involve extending a previously-installed construct to additional vertebral levels by coupling a newly-installed spinal rod to a previously-installed rod. By way of further example, aspects of the patient's anatomy, the surgical technique used, or the desired correction may require that multiple spinal rods be connected to one another. As yet another example, coupling multiple rods to one another can improve the overall strength and stability of an implanted construct.

There can be various difficulties associated with connecting multiple implants to each other. The available space for the implanted construct can often be very limited, particularly in the cervical and/or lumbar areas of the spine. Also, manipulating and handling these relatively small implants at the surgical wound may be challenging or cumbersome for the surgeon. There is a continual need for improved implant connectors and related methods.

SUMMARY

Various rod-to-rod connectors having robust rod closure mechanisms and related methods are disclosed herein, e.g., for enhancing the locking or clamping force applied to a rod. An exemplary connector can be useful to provide a robust rod closure mechanism for rod-to-rod connections in which the run-on rod length of a rod slot is minimal, e.g., less than or equal to 4 millimeters. The connector can include a moveable jaw that is partially disposed within a connector body and configured to pivot or translate relative to the connector body to form a fully closed or substantially closed rod slot around a first rod. The closed rod slot can be formed between a first rod-receiving recess defined in the connector body and a counterpart first rod-receiving recess defined in the moveable jaw. The locking or clamping force of the moveable jaw can be amplified by a mechanical advantage caused by the force exerted to lock a second rod in a second rod-receiving slot of the connector body.

In some embodiments, a rod-to-rod connector can include a connector body defining a first rod-receiving recess and a second rod-receiving slot and a moveable jaw defining a counterpart first rod-receiving recess and moveably coupled to the connector body. The moveable jaw can be configured to move relative to the connector body to form a closed rod slot around a first rod between the first rod-receiving recess and the counterpart first rod-receiving recess in response to a second rod being locked in the second rod-receiving slot.

In some embodiments, the first rod-receiving recess of the connector body can be a distal-facing rod-receiving recess formed in a fixed jaw portion extending laterally from a proximal end of the connector body and the counterpart first rod-receiving recess of the moveable jaw can be a proximal-facing rod-receiving recess. The moveable jaw can be configured to pivot about a first pivot axis of the connector body. The moveable jaw can be configured to pivot clockwise about the first pivot axis to form an open rod slot for receiving the first rod between the distal-facing rod-receiving recess of the fixed jaw portion of the connector body and the proximal-facing rod-receiving recess of the moveable jaw and to pivot counter-clockwise about the first pivot axis to form the closed rod slot around the first rod between the distal-facing rod-receiving recess of the fixed jaw portion of the connector body and the proximal-facing rod-receiving recess of the moveable jaw. Each of the moveable jaw and the fixed jaw portion of the connector body can have a run-on width equal to or less than 4 millimeters.

In some embodiments, the rod-to-rod connector can include a pivot block having a saddle disposed within a cavity formed in a distal end portion of the connector body. The pivot block can be moveably coupled to the connector body and to the moveable jaw, such that the pivot block can pivot about a second pivot axis of the connector body in response to respective movements of the saddle and the moveable jaw. The pivot block can be configured to pivot counter-clockwise about the second pivot axis, thereby raising the saddle into the second rod-receiving slot in response to the moveable jaw pivoting clockwise about the first pivot axis to form the open rod slot for receiving the first rod. The pivot block can be configured to pivot clockwise about the second pivot axis, thereby causing the moveable jaw to pivot counter-clockwise about the first pivot axis to form the closed rod slot around the first rod in response to the second rod exerting a distal force on the saddle of the pivot block. The first rod can be locked within the closed rod slot and the second rod can be locked within the second rod-receiving slot in response to tightening a set screw within a threaded portion of the second rod-receiving slot. The pivot block can be moveably coupled to the moveable jaw by a pin-in-slot connection.

In some embodiments, the moveable jaw can include proximally extending threaded arms forming a proximal-facing threaded recess there between, such that the proximal-facing threaded recess is aligned with a proximal-distal axis of the second rod-receiving slot of the connector body. The moveable jaw can be configured to translate within a cavity formed in the connector body along the proximal-distal axis of the second rod-receiving slot in response to tightening the set screw within the proximal-facing threaded recess of the moveable jaw. The moveable jaw can be configured to translate proximally along the proximal-distal axis of the second rod-receiving slot, and thereby form the closed rod slot around the first rod between the distal-facing rod-receiving recess of the fixed jaw portion of the connector body and the proximal-facing rod-receiving recess of the moveable jaw, in response to tightening the set screw within the proximal-facing threaded recess. The first rod can be locked within the closed rod slot and the second rod can be locked within the second rod-receiving slot in response to tightening the set screw within the proximal-facing threaded recess of the moveable jaw. The moveable jaw can be configured to translate distally along the proximal-distal axis of the second rod-receiving slot, and thereby form an open rod slot between the distal-facing rod-receiving recess of the fixed jaw portion of the connector body and the proximal-facing rod-receiving recess of the moveable jaw. The moveable jaw can be spring-biased to form an open rod slot between the distal-facing rod-receiving recess of the fixed jaw portion of the connector body and the proximal-facing rod-receiving recess of the moveable jaw. The rod-to-rod connector can further include a tongue protruding along at least one of the proximally extending threaded arms and configured to offset a torque exerted by the set screw while tightening the set screw within the proximal-facing threaded recess of the moveable jaw. The moveable jaw can be moveably coupled to the connector body by a pin-in-slot connection.

In some embodiments, the moveable jaw further defines a proximal-facing bearing surface disposed in a cavity formed in the connector body distal to the second rod-receiving slot. The proximal-facing rod bearing surface can be raised into the second rod-receiving slot in response to the moveable jaw pivoting distally to form the open rod slot for receiving the first rod. The moveable jaw can be configured to pivot proximally to form the closed rod slot in response to the second rod exerting a distal force in the second rod-receiving slot on the proximal-facing rod bearing surface of the moveable jaw. The rod-to-rod connector can further include a tooth protruding from an end portion of the moveable jaw and a tooth-receiving pocket formed in a laterally extending jaw of the connector body, such that the tooth of the moveable jaw is configured to interdigitate with the tooth-receiving pocket of the jaw of the connector body.

In some embodiments, the first rod-receiving recess can be an outward-facing rod-receiving recess formed in a fixed jaw portion extending vertically along a lateral face of the connector body and the counter first rod-receiving recess of the moveable jaw can be an inward-facing rod-receiving recess that opposes the outward-facing rod-receiving recess of the fixed jaw portion. The moveable jaw can form a hook at one end that defines the inward-facing rod-receiving recess and a proximal-facing ramped bearing surface protruding at an opposite end. The moveable jaw can be slidably disposed within a tunnel formed in a distal end portion of the connector body between the hook and the ramped bearing surface. The inward-facing rod-receiving recess of the hook and the outward-facing rod-receiving recess of the fixed jaw portion of the connector body can be configured to form an open rod slot for receiving the first rod in response to the moveable jaw sliding in a first axial direction through the tunnel of the connector body. The proximal-facing ramped bearing surface can be configured to enter the second rod-receiving slot of the connector body in response to the moveable jaw sliding in the first axial direction through the tunnel of the connector body. The moveable jaw can be configured to slide in a second axial direction through the tunnel of the connector body and thereby form the closed rod slot around the first rod between the inward-facing rod-receiving recess of the hook and the outward-facing rod-receiving recess of the fixed jaw portion of the connector body. The moveable jaw can be configured to slide in a second axial direction through the tunnel of the connector body in response to the second rod exerting a distal force on the proximal-facing ramped bearing surface and thereby urging the ramped bearing surface out of the second rod-receiving slot. The first rod can be locked within the closed rod slot and the second rod can be locked within the second rod-receiving slot in response to tightening a set screw within the second rod-receiving slot. The moveable jaw can have a cantilevered spring element formed in a distal end of the moveable jaw. The cantilevered spring element can be configured to deflect towards the distal end of the moveable jaw to facilitate insertion of the moveable jaw into the tunnel of the connector body. Each of the moveable jaw and the fixed jaw portion of the connector body can have a run-on width equal to or less than 4 millimeters.

In some embodiments, the moveable jaw can include a swage-receiving slot formed in a distal-facing wall of the moveable jaw and the connector body can include a swaging arm having a swage formed at a free end of the swaging arm. The swaging arm can extend from a bottom wall of the connector body adjacent to the tunnel and can be configured to bend towards the tunnel such that the swage is loosely coupled to the swage-receiving slot. In some embodiments, the moveable jaw can includes one or more swage-receiving slots formed in one or more respective sidewalls of the moveable jaw and the connector body can include one or more swages protruding into the tunnel such that the one or more swages are loosely coupled to the one or more swage-receiving slots of the moveable jaw.

In some embodiments, a method of connecting a first spinal rod and a second spinal rod can include inserting the first spinal rod in a first rod-receiving slot defined between a first rod-receiving recess formed in a connector body of a connector and a counterpart first rod-receiving recess formed in a moveable jaw of the connector and moving the jaw in response to a second rod being locked in a second rod-receiving slot formed in the connector body and thereby closing the first rod-receiving slot around the first rod between the first rod-receiving recess and the counterpart rod-receiving recess such that the connector completely surrounds an outer circumference of the first rod.

In some embodiments, the method can include pivoting the movable jaw clockwise about a first pivot axis to form the first rod-receiving slot for receiving the first rod and pivoting the movable jaw counter-clockwise about the first pivot axis to close the first rod-receiving slot in response to inserting the second rod into the second rod-receiving slot of the connector body. Pivoting the movable jaw counter-clockwise about the first pivot axis to close the first rod-receiving slot in response to inserting the second rod into the second rod-receiving slot of the connector body can include pivoting a pivot block clockwise about a second pivot axis in response to the second rod applying a distal force against a saddle formed on the pivot block and raised into the second rod-receiving slot and pivoting the movable jaw counter-clockwise about the first pivot axis in response to the pivot block pivoting clockwise about the second pivot axis, and thereby closing the first rod-receiving slot about the first rod between the first rod-receiving recess and the counterpart rod-receiving recess. The pivot block can be loosely coupled to the moveable jaw. The method can further include pivoting the pivot block counter-clockwise about the second pivot axis in response to the movable jaw pivoting clockwise about the first pivot axis to form the first rod-receiving slot and thereby raising the saddle of the pivot block into the second rod-receiving slot. The method can further include raising a back end of the movable jaw into the second rod-receiving slot in response to pivoting the movable jaw clockwise about the first pivot axis to form the first rod-receiving slot for receiving the first rod. Pivoting the movable jaw counter-clockwise about the first pivot axis to close the first rod-receiving slot in response to inserting the second rod into the second rod-receiving slot of the connector body can include pivoting the movable jaw counter-clockwise about the first pivot axis to close the first rod-receiving slot in response to the second rod applying a distal force onto the raised back end of the moveable jaw during insertion of the second rod into the second rod-receiving slot.

In some embodiments, the method can include vertically translating the jaw in a proximal direction to form the first rod-receiving slot for receiving the first rod. Moving the jaw in response to the second rod being locked in a second rod-receiving slot formed in the connector body can include vertically translating the jaw in a proximal direction to close the first rod-receiving slot in response to tightening a set screw within a proximal-facing threaded recess of the moveable jaw, such that the proximal-facing threaded recess of the moveable jaw is aligned with the second rod-receiving slot of the connector body.

In some embodiments, the method can include sliding the moveable jaw in a first axial direction away from the connector body to form the first rod-receiving slot between the first rod-receiving recess of the connector body and the counterpart first rod-receiving recess of the moveable jaw, wherein the first axial direction is perpendicular to a proximal-distal axis of the second rod-receiving slot. Moving the jaw in response to the second rod being locked in the second rod-receiving slot can include sliding the moveable jaw in a second axial direction toward the connector body in response to the second rod applying a distal force against a proximal-facing ramped bearing surface that protrudes from a back end of the moveable jaw into the second rod-receiving slot.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of the various embodiments.

DETAILED DESCRIPTION

Figure 1A:
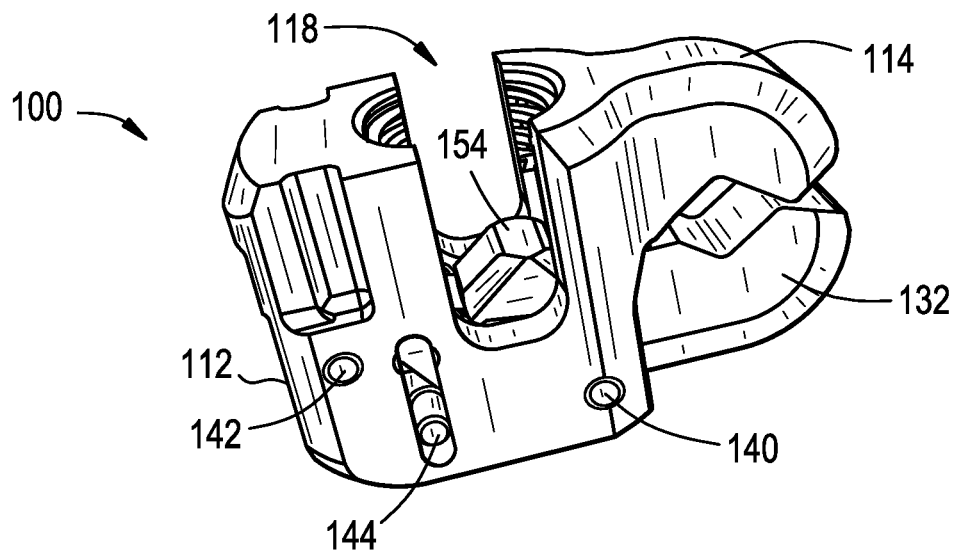
FIGS. 1A and 1B are schematic diagrams illustrating perspective and exploded views of a rod-to-rod connector according to a first embodiment.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

Various embodiments of a rod-to-rod connector are disclosed herein having a rod closure mechanism that enhances the locking or clamping force applied to the rods. The connector may be useful to provide a robust rod closure mechanism for rod-to-rod connections in which the distance between rods is minimized. The connector may be useful to provide a robust rod closure mechanism for rod-to-rod connections in which the run-on rod length of at least one rod slot of the connector is less than or equal to 8 millimeters and preferably less than or equal to 4 millimeters. The connector may include a moveable jaw that is partially disposed within a connector body and configured to pivot or translate relative to the connector body to form a fully closed or substantially closed rod slot around a first rod. The closed rod slot may be formed between a first rod-receiving recess defined in the connector body and a counterpart first rod-receiving recess defined in the moveable jaw. The locking or clamping force of the moveable jaw may be amplified by a mechanical advantage caused by the force exerted to lock a second rod in a second rod-receiving slot of the connector body.

In some embodiments, the mechanical advantage may be provided by a bell crank mechanism in which the moveable jaw is coupled to a pivot block having a saddle disposed within a cavity of the connector body distal to the second rod-receiving slot. To form an open rod slot for receiving a first rod, the moveable jaw is pivoted clockwise about a first pivot axis, thereby causing the pivot block to pivot counter-clockwise about a second pivot axis and raise the saddle into the second rod-receiving slot. Once the first rod is inserted into the open rod slot, a second rod may be inserted into the second rod-receiving slot. The insertion of the second rod may exert a distal force on the saddle of the pivot bock that causes the pivot block to pivot clockwise, and thereby pivot the jaw counter-clockwise to form the closed rod slot around the first rod. By locking the second rod in the second rod-receiving slot with a set screw, the distal force exerted on the saddle may continue to provide a mechanical advantage in the locking force of the moveable jaw.

In some embodiments, the moveable jaw may be configured to translate vertically relative to the connector body without pivoting to form the closed rod slot. The moveable jaw may include a pair of proximally-extending arms that define a proximal-facing threaded recess in alignment with a proximal-distal axis of the second rod-receiving slot. To form the closed rod slot, a set screw may be inserted and tightened within the threaded recess of the moveable jaw. As the screw is tightened, the second rod is pressed against the second rod-receiving slot. Further tightening of the screw may pull the jaw upward into a distal cavity of the connector body until the closed rod slot is formed around the first rod.

In some embodiments, the mechanical advantage may be provided by the moveable jaw itself as a lever. The moveable jaw may include a proximal-facing bearing surface disposed in a cavity formed in the connector body distal to the second rod-receiving slot. To form an open rod slot for receiving a first rod, the moveable jaw may be pivoted clockwise about a first pivot axis, thereby causing the proximal-facing bearing surface to rise into the second rod-receiving slot. Once the first rod is inserted into the open rod slot, a second rod may be inserted into the second rod-receiving slot. The insertion of the second rod may exert a distal force on the proximal-facing bearing surface of the moveable jaw, causing the jaw to pivot counter-clockwise and thereby form the closed rod slot around the first rod. By locking the second rod in the second rod-receiving slot with a set screw, the distal force exerted on the proximal-facing bearing surface of the moveable jaw may continue to provide a mechanical advantage in the locking force of the moveable jaw. The locking or clamping force of the closed rod slot may be further enhanced by configuring opposing ends of the moveable jaw and the fixed jaw portion of the connector body to interdigitate.

In some embodiments, the connector may be configured such that the moveable jaw is slidably disposed within a tunnel formed in a distal end portion of the connector body. The moveable jaw may include a hook defining an inward-facing rod-receiving recess at a front end and a proximal-facing ramped bearing surface protruding at a rear end. To form an open rod slot for receiving the first rod, the jaw may be configured to slide in a first axial direction away from the fixed jaw portion of the connector body. Such axial movement also causes the proximal-facing ramped bearing surface of the jaw to enter the second rod-receiving slot 118. Once the first rod is inserted into the open rod slot, the second rod may be inserted into the second rod-receiving slot. The insertion of the second rod may exert a distal force on the proximal-facing ramped bearing surface, and thereby urge the moveable jaw to slide in a counter-axial direction through the tunnel of the connector body. As the jaw slides in the counter-axial direction, a closed rod slot is formed around the first rod between the inward-facing rod-receiving recess of the hook and the outward-facing rod-receiving recess of the fixed jaw portion of the connector body. By locking the second rod in the second rod-receiving slot with a set screw, a lateral force exerted by the second rod on the ramped bearing surface of the moveable jaw may continue to provide a mechanical advantage in the locking force of the moveable jaw.

In any of the connectors described herein, the first rod slot can be "fully closed", i.e., such that the rod slot completely surrounds an outer circumference of the rod and/or such that opposed jaws of the connector contact each other when a rod is disposed there between. The first rod slot can alternatively be substantially closed, i.e., such that the rod slot surrounds at least about 80% of the circumference of the rod. In any of the connectors described herein, opposing jaws or other components of the first rod slot can be configured to interdigitate with one another when closed around a rod. In any of the connectors described herein, the movable jaw can be biased towards the open position or towards the closed position, e.g., via a spring or other bias element. References herein to "clockwise" and "counterclockwise" directions are taken from the perspective shown in the drawings. It will be appreciated that these directions would be reversed when taken from the opposite perspective.

Figure 1B:
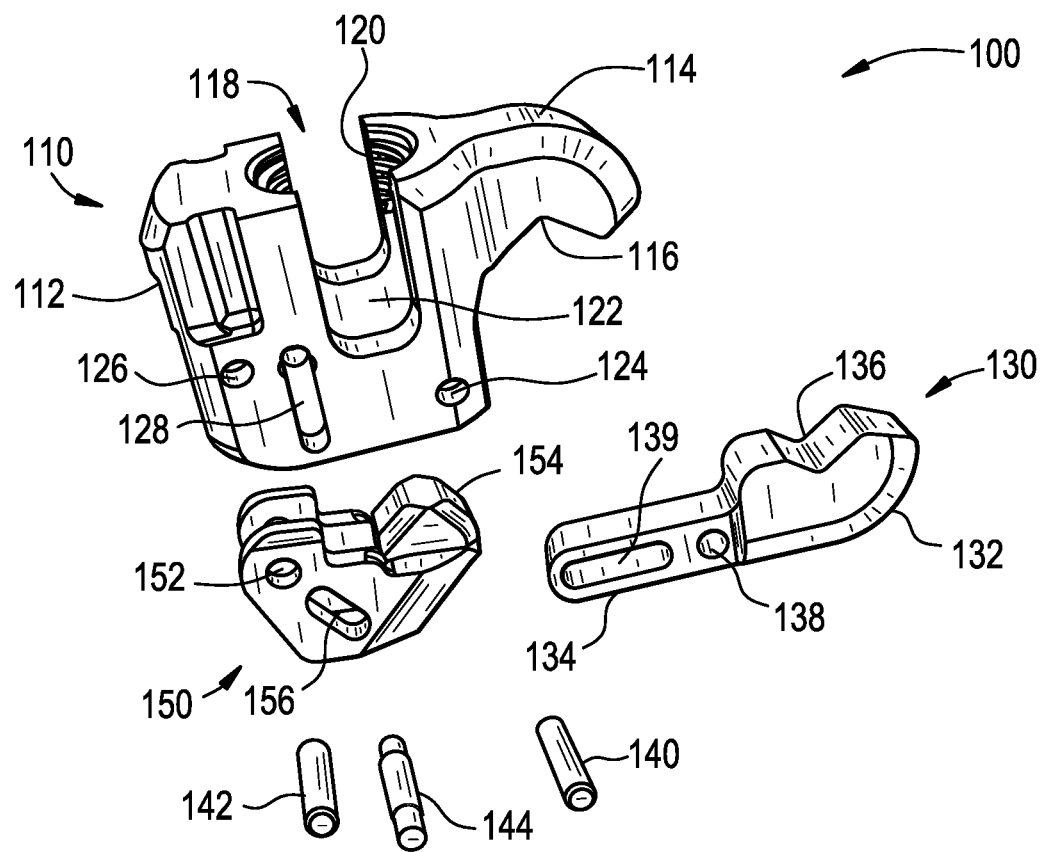

FIGS. 1A and 1B are schematic diagrams illustrating perspective and exploded views of a rod-to-rod connector 100 according to a first embodiment. The connector 100 may include a connector body 110, a moveable jaw 130, and a pivot block 150. The connector body 110 may include a base portion 112 and a fixed jaw portion 114 that extends laterally from a front face of the base portion 112. The base portion 112 may have a substantially cylindrical or other suitable shape to facilitate insertion of the connector 100 at the surgical site (e.g., a vertebral section of the spine). The fixed jaw portion 114 may have an elongated body with a reduced width relative to the base portion 112 of the connector body. The reduced width of the fixed jaw portion 114 may be configured to minimize the run-on rod length of the jaw along a longitudinal axis of the rod. For example, the reduced width of the fixed jaw portion 114 may be less than or equal to 8 millimeters, and preferably less than or equal to 4 millimeters. The elongated body of the fixed jaw portion 114 may have a bent or curved shape conforming to the shape of the rod.

A first rod-receiving recess 116 may formed in a distal-facing surface of the fixed jaw portion 114. The distal-facing, first rod-receiving recess 116 may be a V-shaped, U-shaped, or otherwise contoured groove that forms an upper portion of a lateral-facing (e.g., C-shaped) rod slot for receiving and securing a first rod. The lower portion of the lateral-facing rod slot may be formed by the moveable jaw 130. The lateral-facing rod slot formed there between may be configured to open in response to the moveable jaw 130 pivoting clockwise and to close in response to the jaw pivoting counter-clockwise.

A second rod-receiving slot 118 may be formed in the base portion of the connector body 112. The second rod-receiving slot 118 may be proximal-facing such that the slot opens towards the proximal end of the base portion 112 for receiving and securing a second rod. The second rod-receiving slot 118 may be oriented perpendicular to the laterally extending fixed jaw portion 114 and in parallel to an axis of the first rod-receiving recess 116. The second rod-receiving slot 118 may include a threaded portion 120 configured to threadably receive a set screw for locking the second rod in place.

The moveable jaw 130 may have an elongated body with a front end 132 and a back end 134. The back end of the moveable jaw 134 may be disposed within a distal cavity 122 formed in the base portion of the connector body 112. The front end of the moveable jaw 132 may extend outside the base portion 112 and define a counterpart first rod-receiving recess 136. The counterpart first rod-receiving recess 136 may be formed in a proximal-facing surface at the front end of the moveable jaw 132. The proximal-facing, counterpart first rod-receiving recess 136 may be a V-shaped, U-shaped, or otherwise contoured groove that forms the lower portion of the lateral-facing rod slot for receiving and securing the first rod.

The moveable jaw 130 may be moveably coupled to a distal-front end of the base portion 112 by a first pin 140. The first pin 140, which serves as a pivot axis of the jaw 130, may extend between bores 124 formed in the sidewalls of the base portion 112 and through a bore 138 formed between the front and back ends of the jaw 132 and 134. When the moveable jaw 130 pivots clockwise about the first pin 140, an open rod slot may be formed for receiving a first rod between the distal-facing rod-receiving recess 116 and the proximal-facing rod-receiving recess 136. Conversely, when the moveable jaw pivots counter-clockwise about the first pin 140, a closed rod slot may be formed around the first rod between the distal-facing rod-receiving recess of the fixed jaw portion 116 and the proximal-facing rod-receiving recess of the moveable jaw 136.

To increase the clamping force of the moveable jaw 130 to secure the first rod in place, the back end of the moveable jaw 134 may be loosely coupled to a pivot block 150 disposed within the distal cavity of the connector body 122, forming a bell crank-type mechanism. The pivot block 150 may be moveably coupled to the connector body by a second pin 142, which serves as a pivot axis of the pivot block. The second pin 142 may extend between bores 126 formed in the sidewalls of the base portion 112 and through bores 152 formed in a proximal-back end of the pivot block 150. The pivot block may be capable of pivoting clockwise and counter-clockwise about the second pin 142 within the distal cavity 122.

A saddle 154 may be formed on, or otherwise attached to, a proximal end of the pivot block 150. The saddle 154 may be laterally offset from the pivot axis of the pivot block 150, such that the saddle may be raised from the distal cavity 122 into the second rod-receiving slot 118 in response to a counter-clockwise pivot of the block. The distal end of the pivot block 150 may be loosely coupled to the back end of the moveable jaw 134 by a third pin 144. The third pin 144 may be configured to intersect an obliquely angled slot 156 formed in the pivot block 150 and a horizontal slot 139 of the moveable jaw 130, such that a pivot of the block or jaw causes a counter pivot of the jaw or pivot block, respectively. The third pin 144 is further configured to pass through a vertical slot 128 formed in the sidewall of the base portion of the connector body 112 to guide the pivot and counter-pivot movements of the jaw 130 and pivot block 150.

Figure 2A:
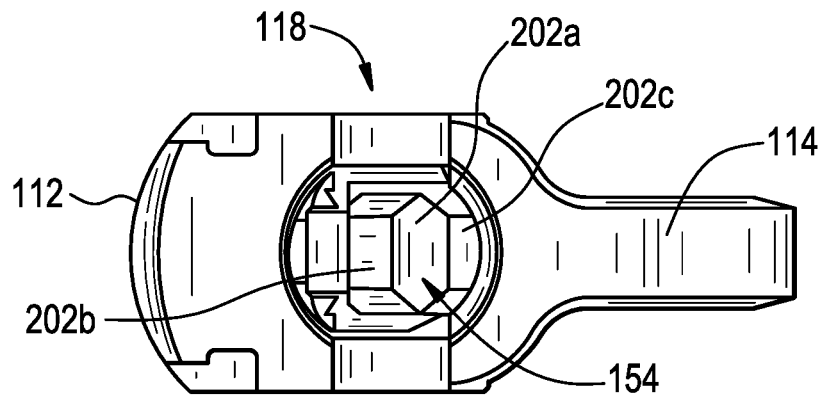
FIGS. 2A, 2B, and 2C are schematic diagrams illustrating top, side, and bottom views of the rod-to-rod connector according to the first embodiment.
Figure 2B:
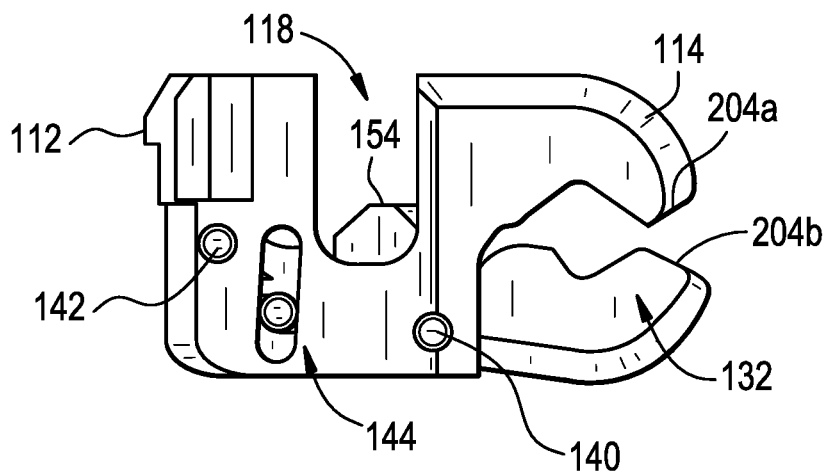
Figure 2C:
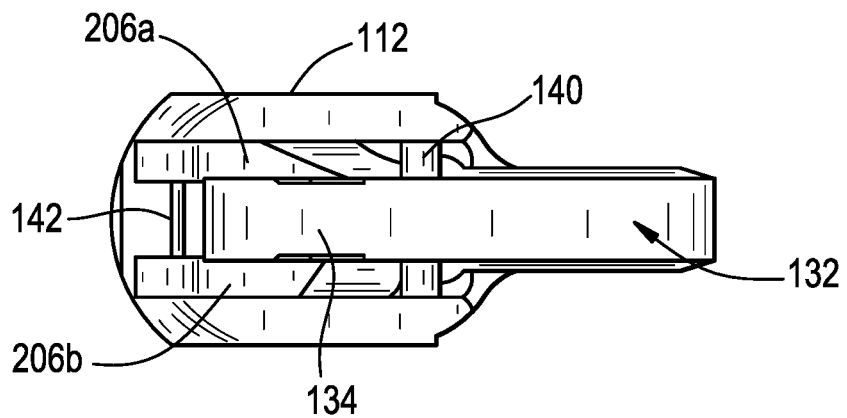

FIGS. 2A, 2B, and 2C are schematic diagrams illustrating top, side, and bottom views of the rod-to-rod connector 100 according to the first embodiment. As shown in FIG. 2A, the saddle 154 of the pivot block 150 may be aligned with the second rod-receiving slot 118, such that the saddle may be raised from the distal cavity 122 into the second rod-receiving slot 118 by a counter-clockwise pivot of the pivot block 150. The saddle 154 may have one or more rod bearing surfaces 202a, 202b, and 202c (collectively 202) on which a second rod may exert a distal force, and thereby cause the pivot block 150 to pivot clockwise about the second pin 142.

As shown in FIG. 2B, opposing lead-in surfaces 204a and 204b (collectively 204) may be formed at the front ends of the fixed jaw portion 114 and the moveable jaw 130 to facilitate insertion of the first rod. The lead-in surfaces of the jaws 204 may be ramped bearing surfaces oriented obliquely at opposite angles to form a V-shaped lead-in. Other lead-in surface configurations may also be used. As the first rod is pushed against the lead-in surfaces 204, the moveable jaw 130 may be urged to pivot clockwise in response thereto, making it easier to open the rod slot formed between the fixed jaw portion 114 and the moveable jaw 130.

As shown in FIG. 2C, the pivot block 150 may include a pair of spaced apart support plates 206a and 206b (collectively 206) that define a cavity there between for receiving the back end of the moveable jaw 134. FIG. 2C further illustrates that the front end of the moveable jaw 132 may have a reduced width relative to the base portion of the connector body 112 to minimize the run-on rod length of the jaw along a longitudinal axis of the first rod. For example, the reduced width of the moveable jaw may be less than or equal to 8 millimeters, and preferably less than or equal to 4 millimeters.

Figure 3A:
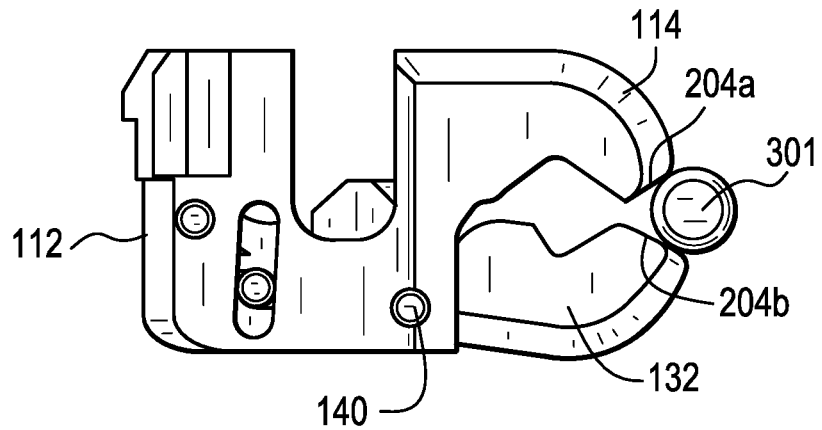
FIGS. 3A through 3F are schematic diagrams illustrating an operation of the rod-to-rod connector according to the first embodiment.
Figure 3B:
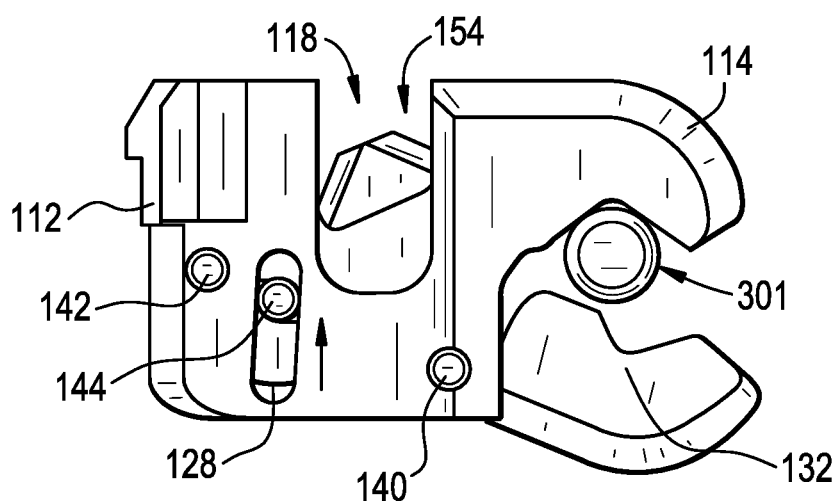
Figure 3C:
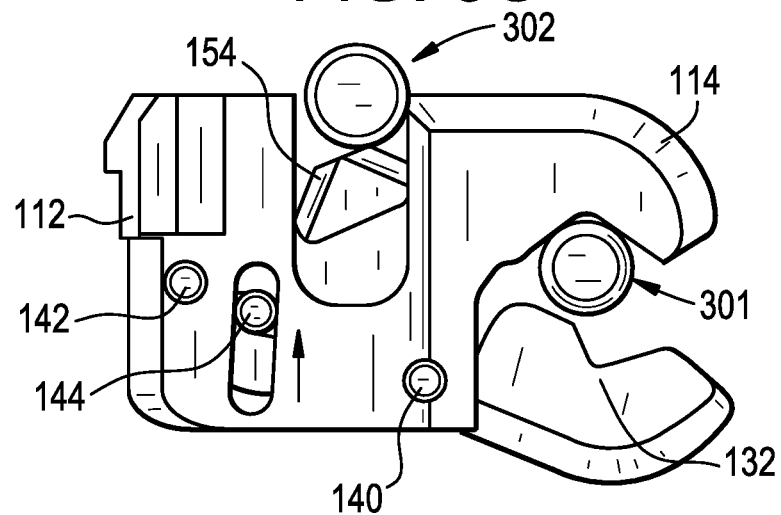
Figure 3D:
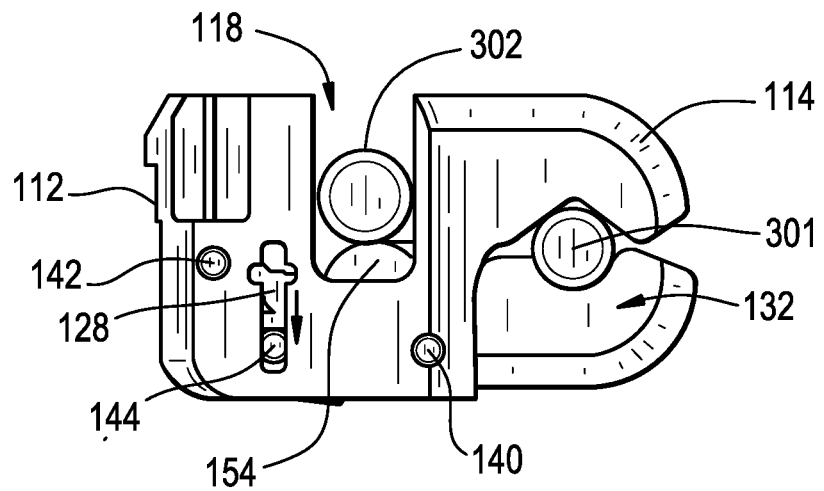
Figure 3E:
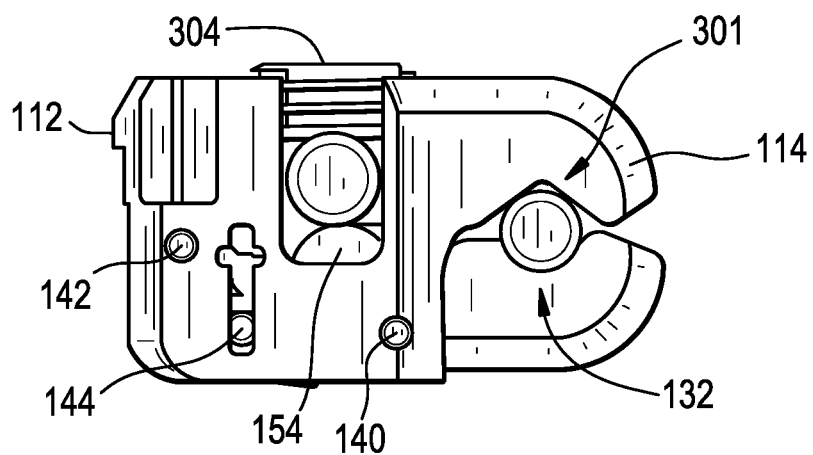
Figure 3F:
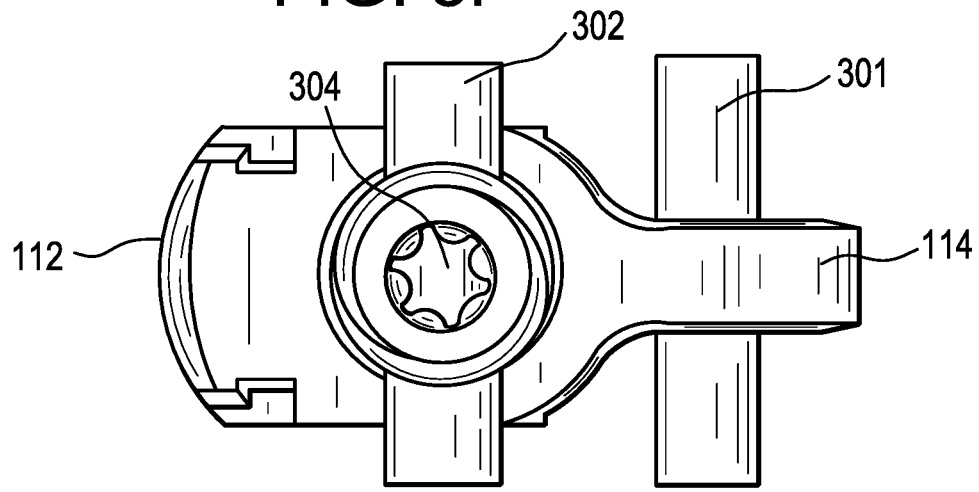

FIGS. 3A through 3F are schematic diagrams illustrating an operation of the rod-to-rod connector 100 according to the first embodiment. As shown in FIG. 3A, a first rod 301 may be pushed against the lead-in surfaces of the jaws 204, thereby urging the moveable jaw to pivot clockwise about the first pin 140. As the moveable jaw pivots clockwise, the front end of the jaw 132 pivots distally to form a lateral-facing, open rod slot for receiving the first rod 301. As shown in FIG. 3B, as the front end of the moveable jaw 132 pivots distally, the back end of the jaw 134 pivots proximally in a clockwise direction, thereby causing the third pin 144 to slide in an upward vertical direction according to the intersecting guide slots 128, 139, and 156 of the connector body, moveable jaw, and pivot block respectively. As the third pin 144 slides vertically up along the guide slot of the connector body 128, the third pin urges against the angled guide slot 156 of the pivot block 150 and causes the block to pivot counter-clockwise about the second pin 142. The counter-clockwise pivot of the block 150 raises the saddle 154 from the distal cavity 122 into the second rod-receiving slot 118. As shown in FIG. 3C, with the first rod 301 inserted in the open rod slot and the saddle 154 in a raised position, a second rod 302 may be inserted into the second rod-receiving slot 118. Pushing down on the second rod 302 exerts a distal force on the saddle of the pivot block 154, thereby causing the pivot block 150 to pivot clockwise about the second pin 142. As shown in FIG. 3D, as the pivot block 150 pivots clockwise, the third pin 144 slides in a downward vertical direction according to the intersecting guide slots 128, 139, and 156 of the connector body, moveable jaw, and pivot block respectively. As the third pin 144 slides downward along the vertical guide slot of the connector body 128, the third pin urges against the horizontal guide slot of the moveable jaw 139, causing the moveable jaw 130 to pivot counter-clockwise about the first pin 140. As the moveable jaw pivots, the front end of the moveable jaw 132 pivots proximally to form a closed rod slot around the first rod 301 between the distal-facing rod-receiving recess of the fixed jaw portion 116 and the proximal-facing rod-receiving recess of the moveable jaw 136. In this way, the distal force exerted on the saddle of the pivot block 154 may be translated into a proximal clamping force of the moveable jaw 130 against the fixed jaw portion 114. As shown in FIG. 3E and FIG. 3F, by tightening a set screw 304 within a threaded portion of the second rod-receiving slot 118, the first rod 301 may be locked within the closed rod slot and the second rod 302 may locked within the second rod-receiving slot 118. Further, by locking the second rod 302 in the second rod-receiving slot 118 with the set screw, the distal force exerted on the saddle 154 may continue to provide a mechanical advantage in the proximal clamping force of the moveable jaw 130.

Figure 4A:
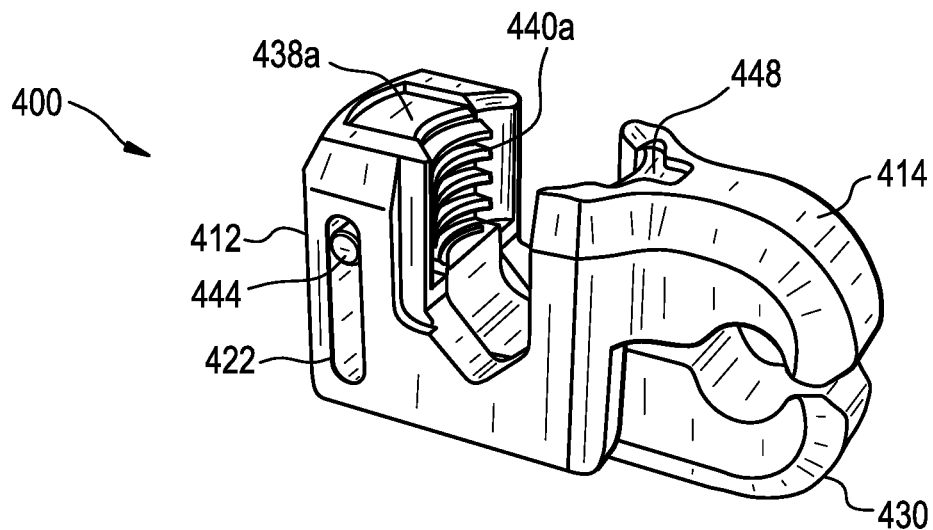
FIGS. 4A and 4B are schematic diagrams illustrating perspective and exploded views of a rod-to-rod connector according to a second embodiment.
Figure 4B:
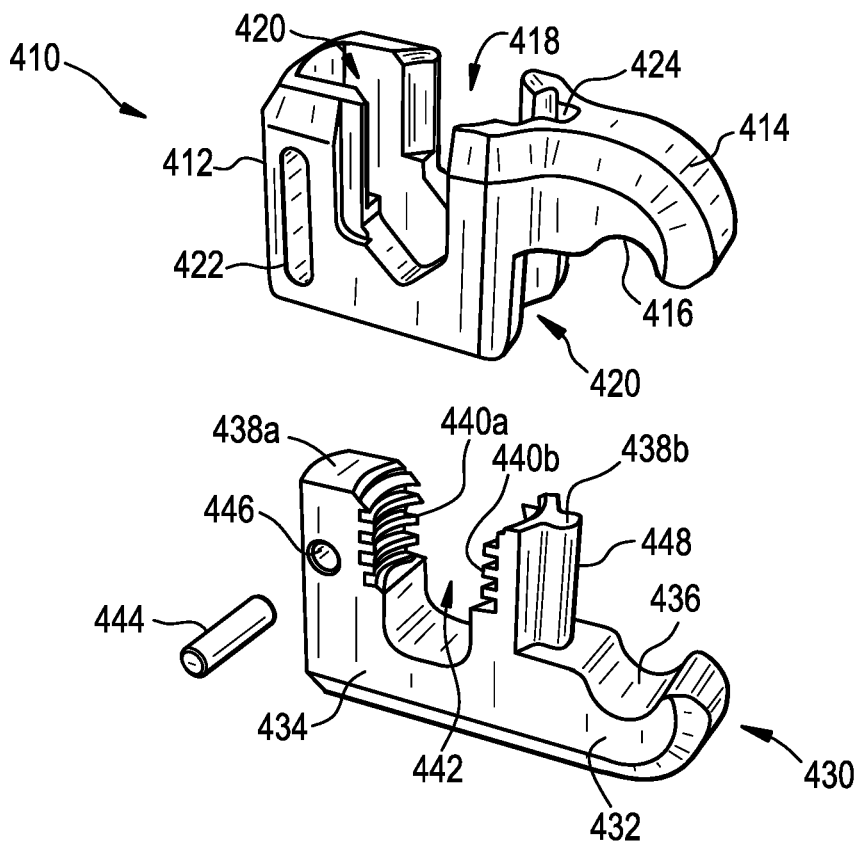

FIGS. 4A and 4B are schematic diagrams illustrating perspective and exploded views of a rod-to-rod connector 400 according to a second embodiment. The connector may include a connector body 410 and a moveable jaw 430. The connector body 410 may include a base portion 412 and a fixed jaw portion 414 that extends laterally from a front face of the base portion. The base portion 412 may have a substantially cylindrical or other suitable shape to facilitate insertion of the connector 400 at the surgical site (e.g., a vertebral section of the spine). The fixed jaw portion 414 may have an elongated body with a reduced width relative to the base portion of the connector body 412 to minimize the run-on rod length of the jaw along a longitudinal axis of the rod. For example, the reduced width of the fixed jaw portion 414 may be less than or equal to 8 millimeters, and preferably less than or equal to 4 millimeters. The elongated body of the fixed jaw portion 414 may be distally bent or curved.

A first rod-receiving recess 416 may be formed in a distal-facing surface of the fixed jaw portion 414. The distal-facing, first rod-receiving recess 416 may be a V-shaped, U-shaped, or otherwise contoured groove configured to form an upper portion of a lateral-facing (e.g., C-shaped) rod slot for receiving and securing a first rod. The lower portion of the lateral-facing rod slot may be formed in a proximal-facing surface of the moveable jaw 430. The lateral-facing rod slot formed there between may be configured to open in response to the moveable jaw 430 vertically translating in a distal direction away from the connector body 410 and to close in response to the moveable jaw 430 vertically translating in a proximal direction towards the connector body 410.

A second rod-receiving slot 418 may be formed in the base portion of the connector body 412. The second rod-receiving slot 418 may be proximal-facing such that the slot opens towards the proximal end of the base portion 412 for receiving and securing a second rod. The second rod-receiving slot 418 may be oriented perpendicular to the laterally extending fixed jaw portion 414 and in parallel to an axis of the first rod-receiving recess 416.

The moveable jaw 430 may have an elongated body having a front end 432 and a back end 434. A counterpart first rod-receiving recess 436 may be formed in a proximal-facing surface at the front end of the jaw 432 that extends outside the base portion of the connector body 412. The proximal-facing, counterpart first rod-receiving recess 436 may be a V-shaped, U-shaped, or otherwise contoured groove configured to form a lower portion of the lateral-facing (e.g., C-shaped) rod slot configured to receive and secure a first rod. The back end 434 of the moveable jaw may include at least two proximally extending arms 438a and 438b (collectively 438) configured to vertically translate within a cavity 420 formed in the base portion of the connector body 412. The opposing faces of the arms 440a and 440b (collectively 440) may have a threaded portion formed at the proximal ends thereof, forming a proximal-facing threaded recess 442 there between. The proximal-facing threaded recess 442 may be aligned with a proximal-distal axis of the second rod-receiving slot of the connector body 418. The threaded portion of the opposing arms 440 may be configured to threadably receive a set screw that, when tightened, causes the moveable jaw 430 to vertically translate within the cavity 420 in a proximal direction. The arms 438 can include reduction or extension tabs that extend proximally therefrom, e.g., to a location outside the patient's body, to functionally extend the length of the arms and facilitate insertion of the set screw. The extension tabs can be threaded. The extension tabs can be configured to break off or otherwise separate from the connector prior to completing the surgical procedure.

The moveable jaw 430 may be moveably coupled to the connector body 410, such that the jaw may be configured to vertically translate along the proximal-distal axis of the second rod-receiving slot within the cavity 420 formed therein. As shown, the moveable jaw 430 may be moveably coupled to the connector body by a pin 444 extending from the back arm of the moveable jaw 438a through a vertical guide slot 422 formed in a sidewall of the connector body 410. The pin 444 may be press fit or otherwise fixedly coupled in a bore 446 formed in the back arm of the moveable jaw 438a. The proximally extending front arm 438b of the moveable jaw 430 may include a tongue protrusion 448 formed along a front face of the arm 438b to slideably engage a counterpart groove 424 formed base portion of the connector body 412.

Figure 5A:
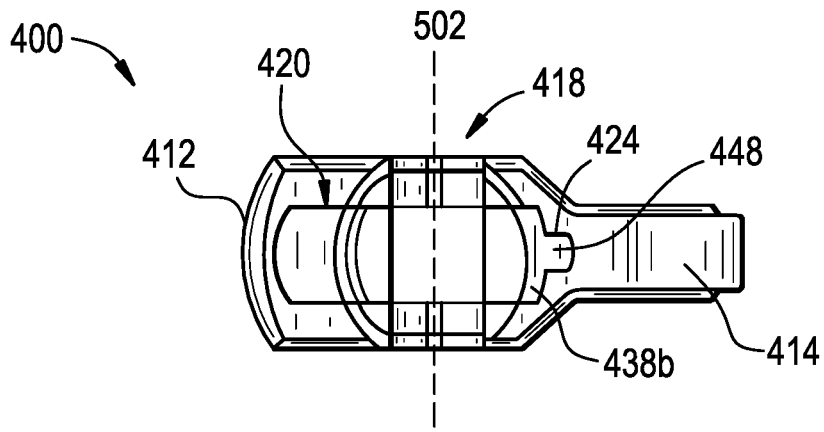
FIGS. 5A, 5B, and 5C are schematic diagrams illustrating top, side, and bottom views of the rod-to-rod connector according to the second embodiment.
Figure 5B:
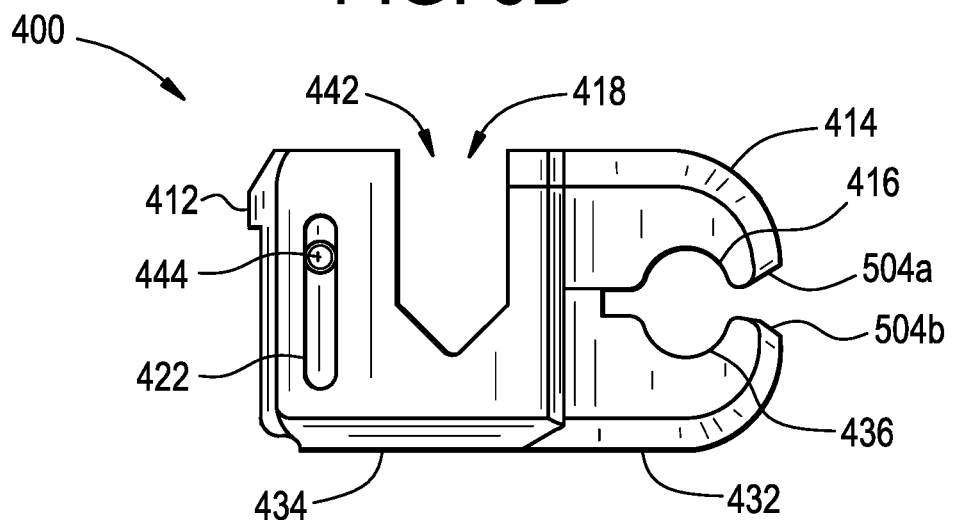
Figure 5C:
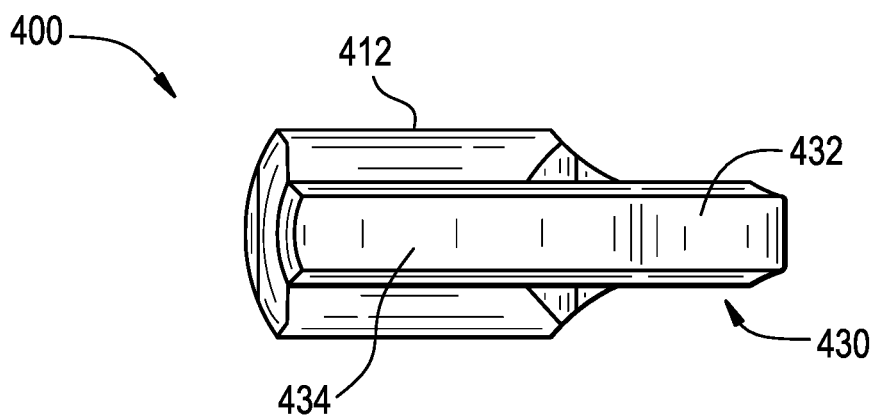

FIGS. 5A, 5B, and 5C are schematic diagrams illustrating top, side, and bottom views of the rod-to-rod connector 400 according to the second embodiment. As shown in FIG. 5A, the base portion of the connector body 412 may define a cavity 424 that conforms to the external shape of the proximally extending arms 438 of the moveable jaw 430. The cavity 420 may extend between the proximal and distal ends of the base portion of the connector body 412. The groove 424 may be configured to slideably engage the tongue protrusion 448 of the forward arm of the jaw 438b to provide additional support and prevent twisting of the forward arm as a torque is applied to tighten the screw (not shown) within the proximal-facing threaded recess 442. FIG. 5A further illustrates that the proximal-facing threaded recess 442 may be aligned with a rod-receiving axis 502 of the second rod-receiving slot 418.

As shown in FIG. 5B, opposing lead-in surfaces 504a and 504b (collectively 504) may be formed at the front ends of the fixed jaw portion 414 and the moveable jaw 430 to facilitate insertion of the first rod. The lead-in surfaces of the jaws 504 may be ramped bearing surfaces oriented obliquely at opposite angles to form a V-shaped lead-in. Other lead-in surface configurations may also be used. As the first rod being pushed against the lead-in surfaces 504, the moveable jaw 430 may be urged to translate vertically in a distal direction in response thereto, making it easier to open the rod slot between the fixed jaw portion 414 and the moveable jaw 430.

FIG. 5C illustrates that the moveable jaw 430 may have an elongated body with a reduced width relative to the base portion of the connector body 412 to minimize the run-on rod length of the jaw along a longitudinal axis of the first rod. For example, the reduced width of the moveable jaw 430 may be less than or equal to 8 millimeters, and preferably less than or equal to 4 millimeters.

Figure 6A:
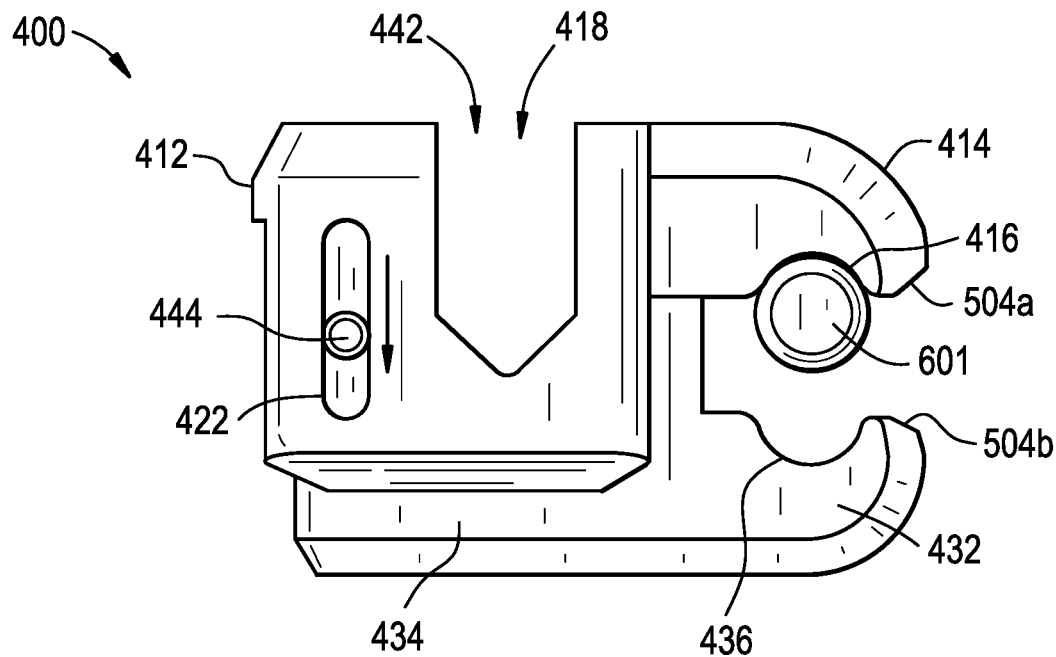
FIGS. 6A through 6D are schematic diagrams illustrating an operation of the rod-to-rod connector according to the second embodiment.

FIGS. 6A through 6D are schematic diagrams illustrating an operation of the rod-to-rod connector 400 according to the second embodiment. As shown in FIG. 6A, the moveable jaw 430 is initially positioned within the cavity of the connector body 420 such that the front end of the moveable jaw 432 is separated from the fixed jaw portion of the connector body 414 to form an open rod slot for receiving the first rod 601. The moveable jaw 430 may be spring-biased to a distally lowered position within the cavity 420 to form the open rod slot in a default resting configuration. The moveable jaw 430 may be mechanically lowered by pushing the first rod 601 against the lead-in surfaces of the jaws 504, and thereby urging the moveable jaw 430 to translate vertically in the distal direction. The vertical translation of the jaw 430 may be guided by the pin 444 sliding along the vertical guide slot 422 formed in the base portion of the connector body 412.

Figure 6B:
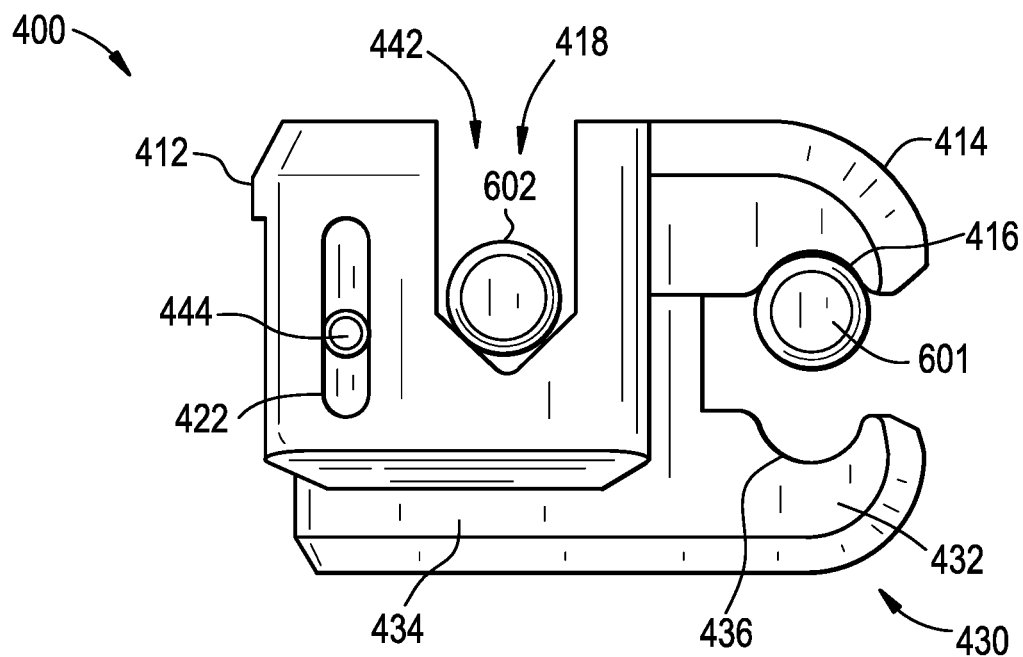
Figure 6C:
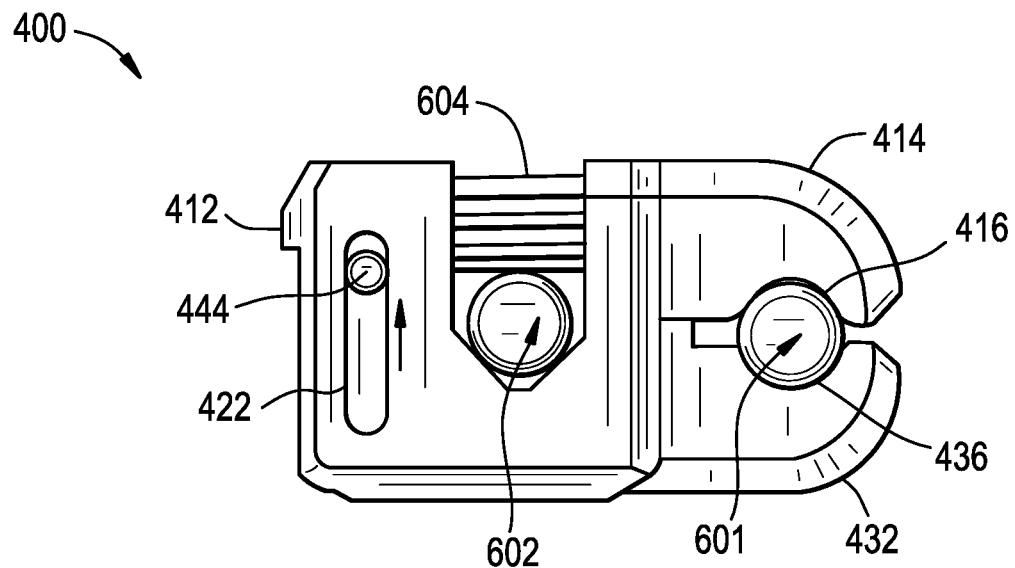
Figure 6D:
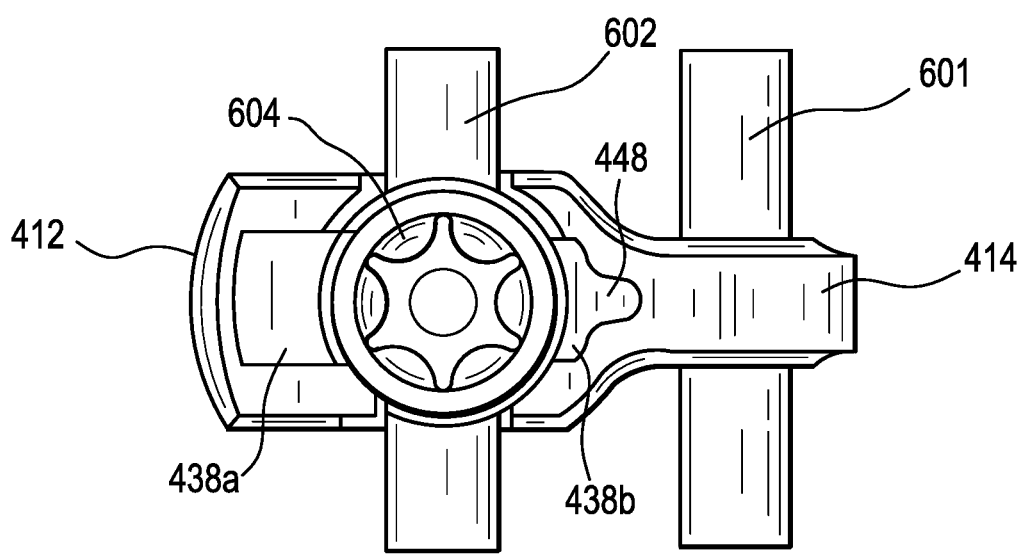

As shown in FIG. 6B, a second rod 602 may be inserted in the second rod-receiving slot 418 after the first rod 601 is inserted into the open rod slot formed between the fixed jaw portion 414 and the front end of the moveable jaw 432. The second rod 602 may also be inserted in the second rod-receiving slot 418 before or concurrently with the insertion of the first rod 601 in the open rod slot formed between the jaws. As shown in FIGS. 6C and 6D, a set screw 604 may be inserted into the proximal-facing threaded recess 442 that is formed between the arms of the moveable jaw 438 and coaxial with the second rod-receiving slot 418. As the screw 604 is tightened, the second rod 604 presses against the base of the second rod-receiving slot 418. Further tightening of the screw 604 pulls the moveable jaw 430 upward such that the jaw vertically translates in a proximal direction into the cavity 420. The screw 604 may continue to be tightened until the first rod-receiving recess of the fixed jaw portion 416 and the counterpart first rod-receiving recess of the moveable jaw 436 form a closed rod slot around the first rod 601.

Figure 7A:
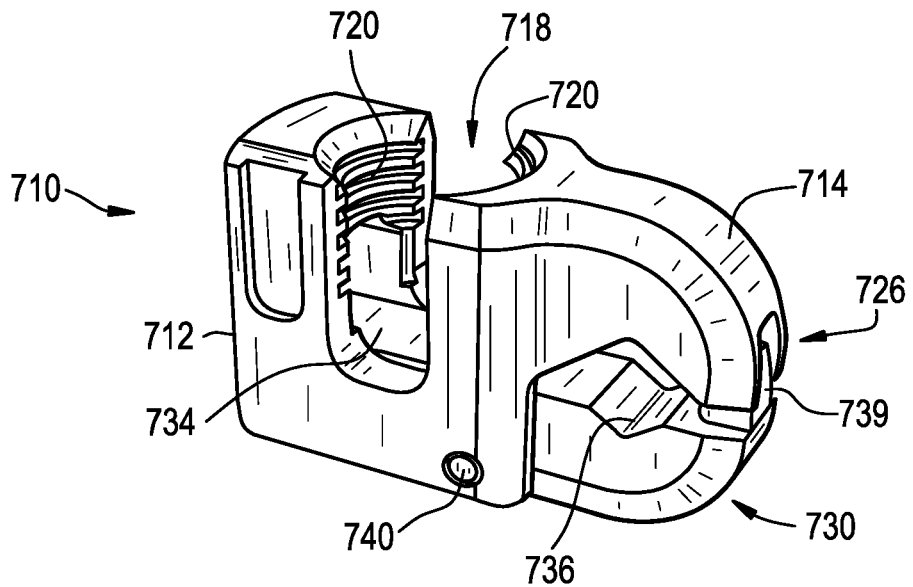
FIGS. 7A and 7B are schematic diagrams illustrating perspective and exploded views of a rod-to-rod connector according to a third embodiment.
Figure 7B:
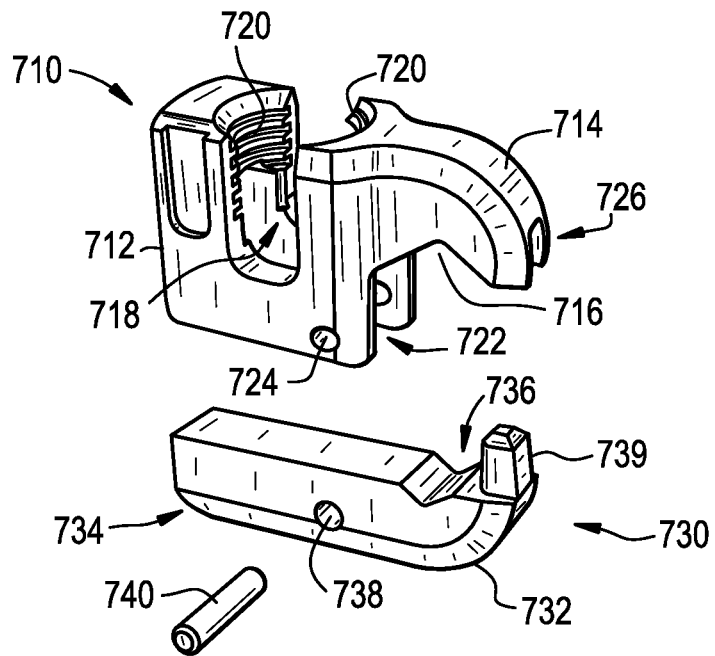

FIGS. 7A and 7B are schematic diagrams illustrating perspective and exploded views of a rod-to-rod connector 700 according to a third embodiment. The connector 700 may include a connector body 710 and a moveable jaw 730.

The connector body 710 may include a base portion 712 and a fixed jaw portion 714 that extends laterally from a front face of the base portion. The base portion 712 may have a substantially cylindrical or other suitable shape to facilitate insertion of the connector 700 at the surgical site (e.g., a vertebral section of the spine). The fixed jaw portion 714 may have an elongated body with a reduced width relative to the base portion of the connector body 712 to minimize the run-on rod length of the jaw along a longitudinal axis of the rod. For example, the reduced width of the fixed jaw portion 714 may be less than or equal to 8 millimeters, and preferably less than or equal to 4 millimeters. The elongated body of the fixed jaw portion 714 may be distally bent or curved.

A first rod-receiving recess 716 may formed in a distal-facing surface of the fixed jaw portion 714. The distal-facing, first rod-receiving recess 716 may be a V-shaped, U-shaped, or otherwise contoured groove configured to form an upper portion of a lateral-facing (e.g., C-shaped) rod slot that is configured to receive and secure a first rod (not shown). The lower portion of the lateral-facing rod slot may be formed in a proximal-facing surface of the moveable jaw 730. The lateral-facing rod slot formed there between may be configured to open in response to the moveable jaw 730 pivoting clockwise and to close in response to the moveable jaw 730 pivoting counter-clockwise.

A second rod-receiving slot 718 may be formed in the base portion of the connector body 712. The second rod-receiving slot 718 may be proximal-facing such that the slot opens towards the proximal end of the base portion 712 for receiving and securing a second rod. The second rod-receiving slot 718 may be oriented perpendicular to the laterally extending fixed jaw portion 714 and in parallel to an axis of the first rod-receiving recess 716. The second rod-receiving slot 718 may include a threaded portion 720 configured to threadably receive a set screw (not shown) for locking the second rod in the slot.

The moveable jaw 730 may have an elongated body with a front end 732 and a back end 734. The back end of the moveable jaw 734 may be disposed within a distal cavity 722 formed in the base portion of the connector body 712. The front end of the moveable jaw 732 may extend outside the base portion 712 and define a counterpart first rod-receiving recess 736. The counterpart first rod-receiving recess 736 may be formed in a proximal-facing surface at the front end of the jaw 732. The proximal-facing, counterpart first rod-receiving recess 736 may be a V-shaped, U-shaped, or otherwise contoured groove configured to form a lower portion of the lateral-facing (e.g., C-shaped) rod slot configured to receive and secure a first rod.

The moveable jaw 730 may be moveably coupled to a distal-front end of the base portion 712 by a pin 740 between the first and second ends of the jaw. The pin 740, which serves as a pivot axis of the moveable jaw 730, may extend between bores 724 formed in the sidewalls of the base portion 712 and through a bore 738 formed between the front and back ends of the jaw 732 and 734. When the moveable jaw 730 pivots clockwise about the pin 740, an open rod slot may be formed for receiving the first rod between the distal-facing rod-receiving recess of the fixed jaw portion 716 and the proximal-facing rod-receiving recess of the moveable jaw 736. Conversely, when the moveable jaw 730 pivots counter-clockwise about the pin 740, a closed rod slot may be formed around the first rod between the distal-facing rod-receiving recess 716 and the proximal-facing rod-receiving recess 736.

To prevent the first rod from becoming displaced from the closed rod slot (e.g., popping out), the jaws of the connector may be configured to interdigitate with each other. As shown, a proximally-extending tooth 739 may be formed on a proximal surface of the front end of the moveable jaw 732 to interdigitate with a distal-facing, tooth-receiving pocket 726 formed in the fixed jaw portion of the connector body 714. The tooth 739 may have a substantially rectangular or other suitable shape that may be received in the pocket 726. The tooth 739 may have a width that is narrower than the width of the fixed jaw portion 714. The tooth-receiving pocket 726 may be open distally and laterally toward the front of the fixed jaw portion 714, such that the tooth 739 may be pivoted into the pocket as the moveable jaw 730 pivots counter-clockwise to form the closed rod slot. Although the tooth as shown is formed on the moveable jaw, the interdigitating arrangement may be flipped. For example, a distal-facing tooth may be formed on a distal surface of the fixed jaw portion and a proximal-facing tooth-receiving pocket may be formed in the proximal surface of the moveable jaw. The tooth and tooth-receiving pocket may optionally be incorporated into any of the other embodiments rod-to-rod connectors disclosed herein (e.g., connectors 100, 400, and 1000). While a single tooth and a single pocket are shown, in other arrangements the connector can include a plurality of interdigitating features.

Figure 8A:
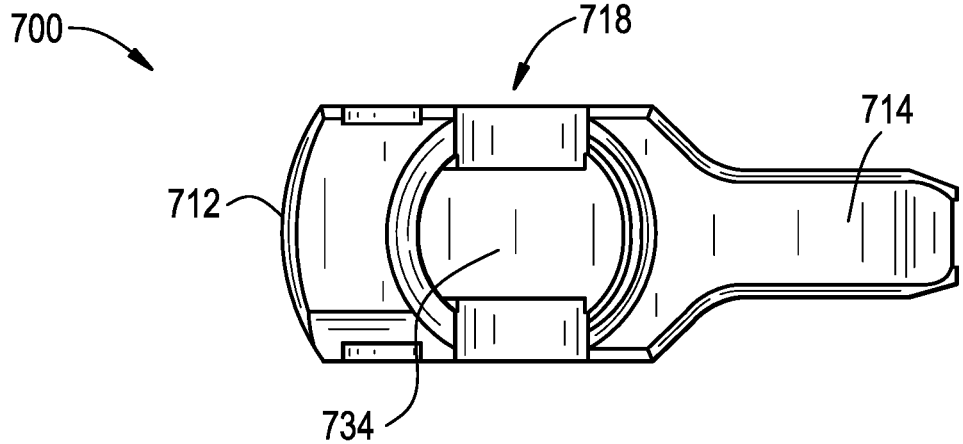
FIGS. 8A, 8B, and 8C are schematic diagrams illustrating top, side, and bottom views of the rod-to-rod connector according to the third embodiment.
Figure 8B:
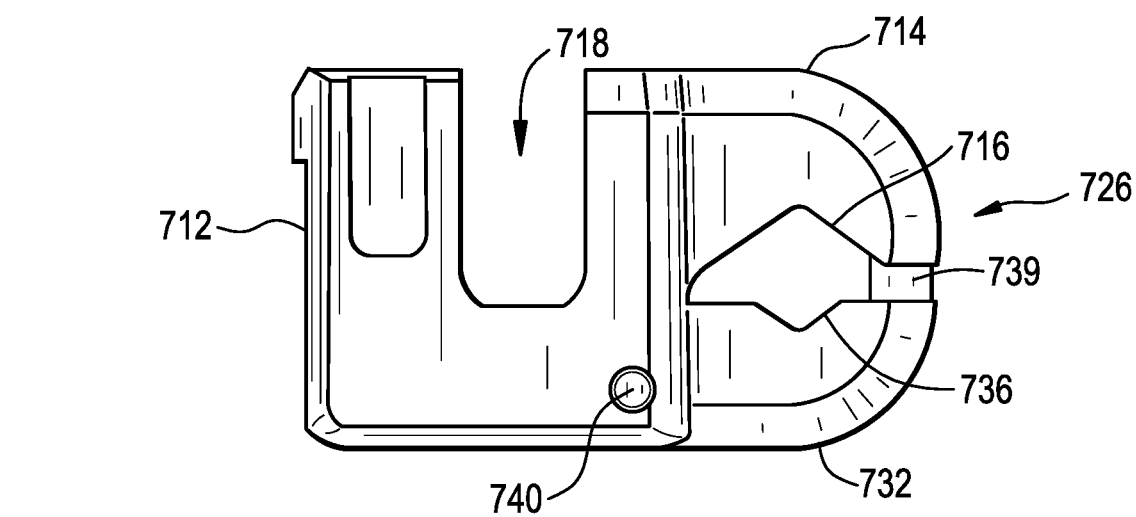
Figure 8C:
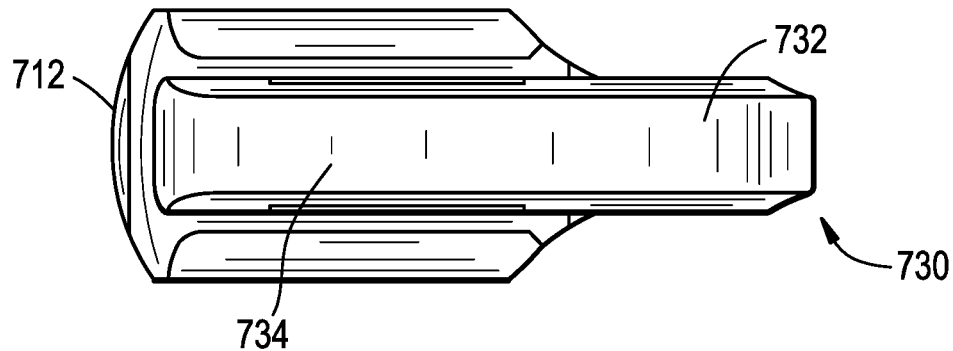

FIGS. 8A, 8B, and 8C are schematic diagrams illustrating top, side, and bottom views of the rod-to-rod connector 700 according to the third embodiment. As shown in FIG. 8A, the back end of the moveable jaw 734 may be aligned with the second rod-receiving slot of the connector body 718, such that the back end of the jaw may be raised from the distal cavity of the connector body 722 into the second rod-receiving slot 718 by a clockwise pivot of the moveable jaw 730 about the pin 740. As shown in FIG. 8B, the proximal-facing tooth 739 protruding from the front end of the moveable jaw 732 may be configured to interdigitate with the tooth-receiving pocket of the fixed jaw portion 726 such that the rod slot formed there between may be completely closed, with no separation between the front ends (or tips) of the jaws. As shown in FIG. 8C, the moveable jaw 730 may have an elongated body with a reduced width relative to the base portion of the connector body to minimize the run-on rod length of the jaw along a longitudinal axis of the first rod. For example, the reduced width of the moveable jaw 730 may be less than or equal to 8 millimeters, and preferably less than or equal to 4 millimeters.

Figure 9A:
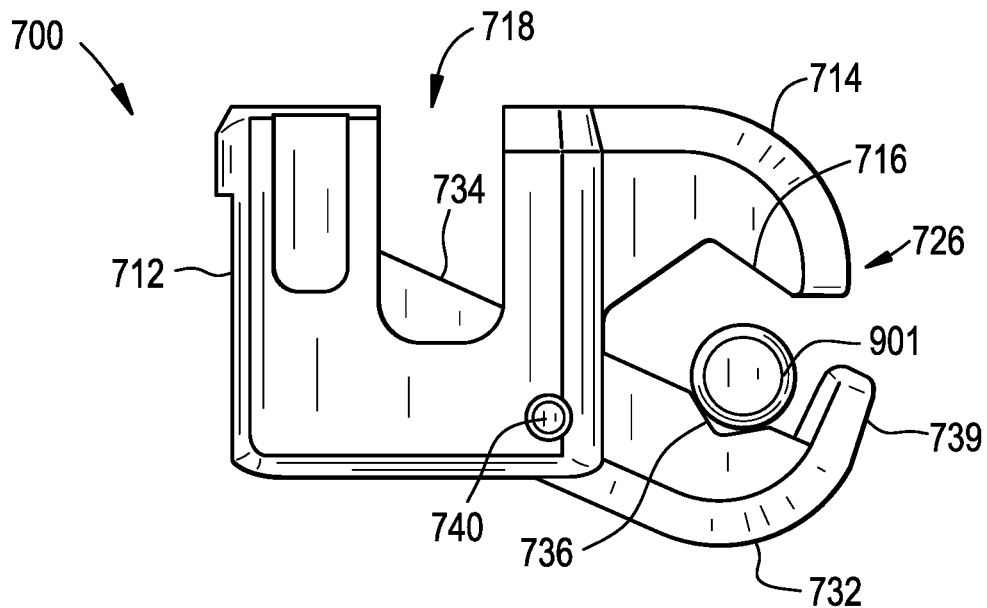
FIGS. 9A through 9D are schematic diagrams illustrating an operation of the rod-to-rod connector according to the third embodiment.
Figure 9B:
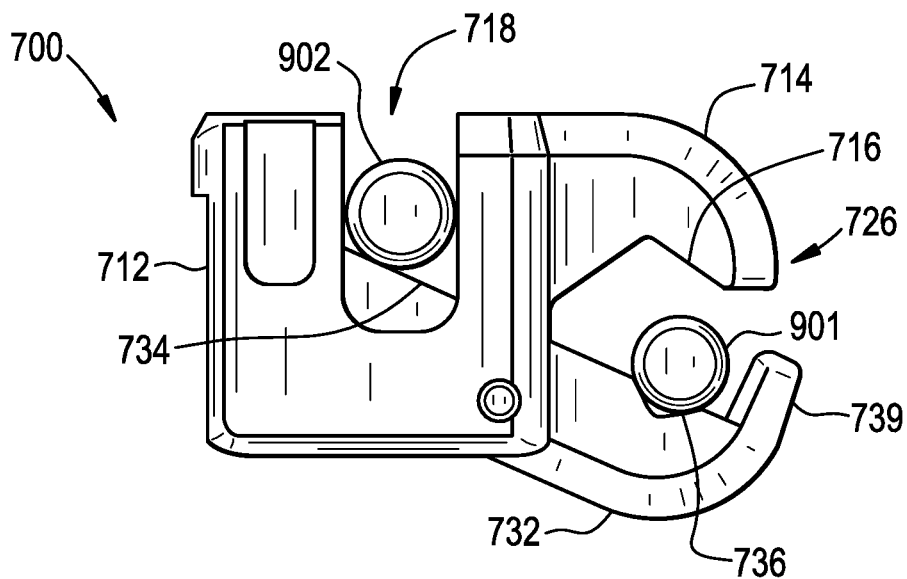
Figure 9C:
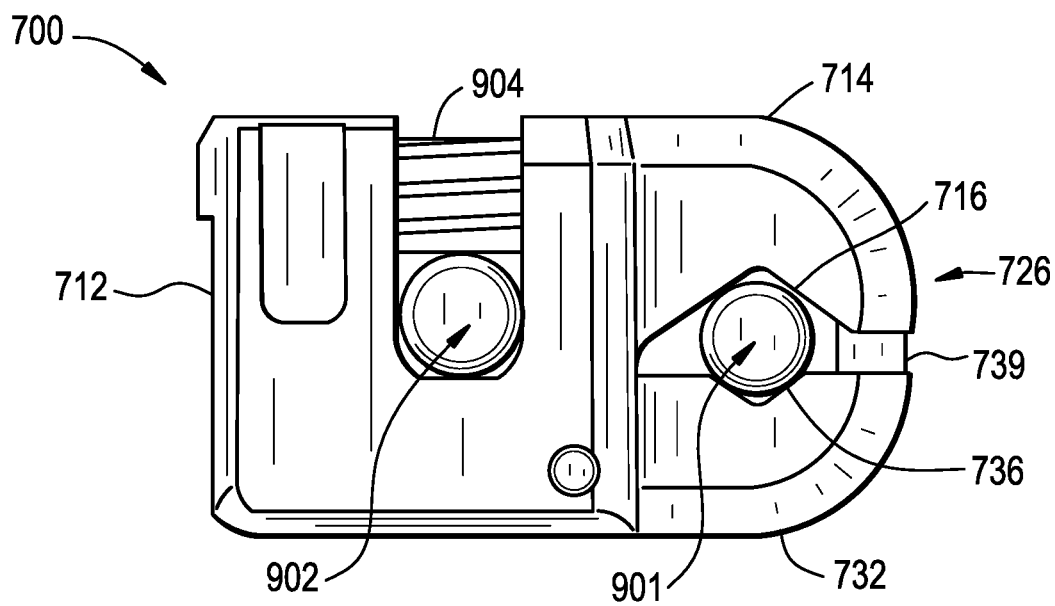
Figure 9D:
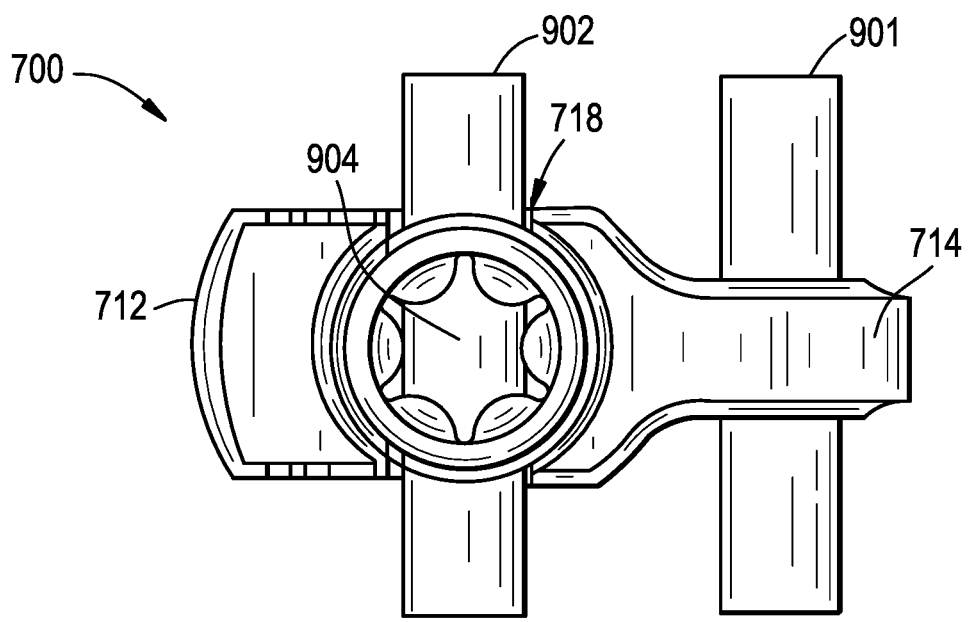

FIGS. 9A through 9D are schematic diagrams illustrating an operation of the rod-to-rod connector 700 according to the third embodiment. As shown in FIG. 9A, to form a lateral-facing, open rod slot for receiving the first rod 901, the moveable jaw 730 is pivoted clockwise, thereby disengaging the tooth of the moveable jaw 739 from the tooth-receiving pocket of the fixed jaw portion 726. As shown in FIG. 9B, as the front end of the moveable jaw 732 pivots distally, the back end of the jaw 734 pivots proximally in a clockwise direction, and thereby rises from the distal cavity into the second rod-receiving slot 718. As shown in FIG. 9B, with the first rod 901 inserted in the open rod slot and the back end of the moveable jaw 734 raised into the second rod-receiving slot 718, a second rod 902 may be inserted into the second rod-receiving slot 718. Pushing down on the second rod 902 exerts a distal force on the back end of the jaw 734, thereby causing the moveable jaw 730 to pivot counter-clockwise. As shown in FIGS. 9C and 9D, as the moveable jaw 730 pivots counter-clockwise, the front end of the jaw 732 pivots proximally to form a closed rod slot around the first rod 901 between the distal-facing rod-receiving recess of the fixed jaw portion 716 and the proximal-facing rod-receiving recess of the moveable jaw 736. In this closed configuration, the proximally-extending tooth of the moveable jaw 739 interdigitates with the tooth-receiving pocket of the fixed jaw portion 726. Thus, the moveable jaw 730 may act as a lever in which the distal force exerted on the back end of the moveable jaw 734 by the second rod 902 provides a mechanical advantage in generating the proximal clamping force of the front end of the moveable jaw 732 against the fixed jaw portion. Further, by tightening a set screw 904 within a threaded portion of the second rod-receiving slot 718, the first rod 901 may be locked within the closed rod slot simultaneously with the second rod 902 being locked within the second rod-receiving slot 718. By locking the second rod 902 in the second rod-receiving slot 718 with a set screw 904, the distal force exerted by the second rod 902 on the back end of the moveable jaw 734 may continue to provide a mechanical advantage in the proximal clamping force of the front end of the moveable jaw 732 against the fixed jaw portion.

Figure 10A:
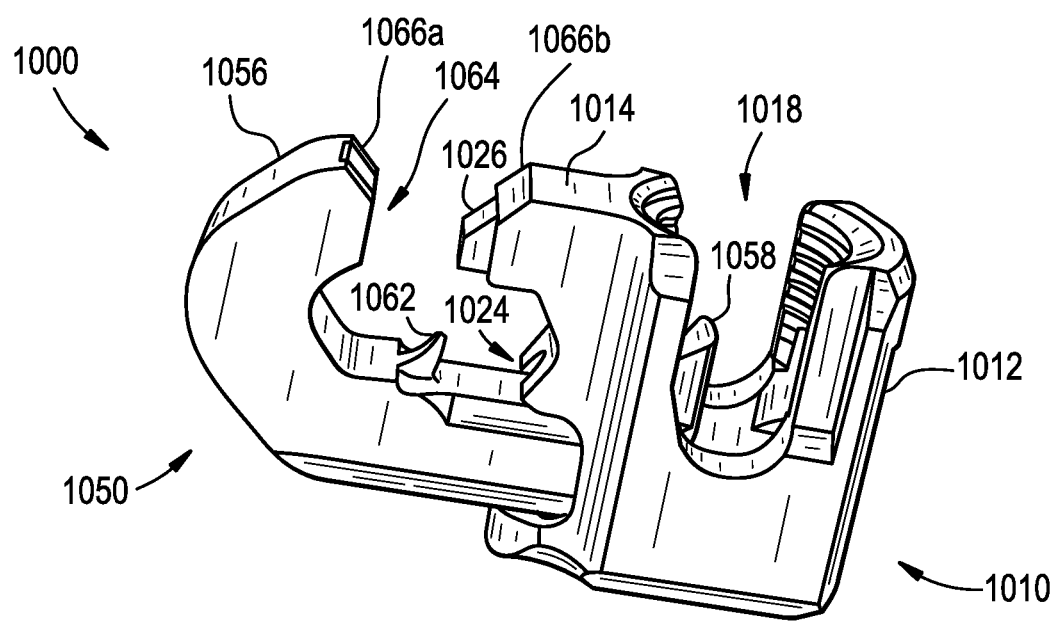
FIGS. 10A and 10B are schematic diagrams illustrating perspective and exploded views of a rod-to-rod connector according to a fourth embodiment.
Figure 10B:
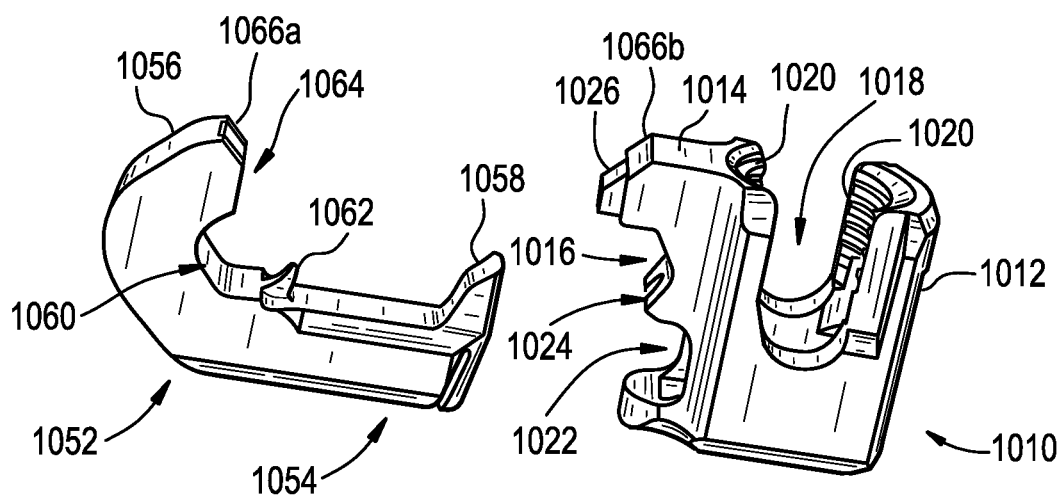

FIGS. 10A and 10B are schematic diagrams illustrating perspective and exploded views of a rod-to-rod connector 1000 according to a fourth embodiment. The connector 1000 may include a connector body 1010 and a moveable jaw 1050.

The connector body 1010 may include a base portion 1012 and a fixed jaw portion 1014 that extends vertically along a front-lateral face of the base portion. The base portion 1012 may have a substantially cylindrical or other suitable shape to facilitate insertion of the connector 1000 at the surgical site (e.g., a vertebral section of the spine). The fixed jaw portion 1014 may form an outward-facing, first rod-receiving recess 1016 in a front-lateral surface thereof. The outward-facing, first rod-receiving recess 1016 may be a V-shaped, U-shaped, or otherwise contoured groove configured to form part of a proximal-facing (e.g., U-shaped) rod slot that is configured to receive and secure a first rod.

A second rod-receiving slot 1018 may be formed in the base portion of the connector body 1012. The second rod-receiving slot 1018 may be proximal-facing such that the slot opens towards the proximal end of the base portion 1012 for receiving and securing a second rod. The second rod-receiving slot 1018 may include a threaded portion 1020 configured to threadably receive a set screw for locking the second rod in the slot.

The moveable jaw 1050 may be an elongated body having a front end 1052 and a back end 1054. A hook 1056 may be formed at the front end 1052 and a proximal-facing ramped bearing surface 1058 protrudes at the back end 1054. An inner surface of the hook may form an inward-facing, first rod-receiving recess 1060 configured to oppose the outward-facing, first rod-receiving recess of the fixed jaw portion 1016. The moveable jaw may be slidably disposed within a tunnel 1022 formed in a distal end of the base portion 1012 between the hook 1056 and the ramped bearing surface 1058. The moveable jaw 1050 may be configured to slide along the tunnel 1022 to form a proximal-facing open or closed rod slot between the inward-facing first rod-receiving recess of the hook 1060 and the outward-facing rod-receiving recess of the fixed jaw portion 1016.

The moveable jaw 1050 may also include a stop tab 1062 that protrudes from a proximal surface between the hook 1056 and the ramped bearing surface 1058. The stop tab 1062 may be configured to engage a counterpart pocket 1024 formed in a surface of the fixed jaw portion 1014. The stop tab 1062 may protrude from a position on the surface of the jaw 1050, such that the stop tab engages the counterpart pocket 1024 when the jaw moves into the closed rod slot configuration. The stop tab 1062 may have a "shark fin" or other suitable shape configured to counter torque and/or to otherwise strengthen the clamping force of the jaws around the first rod in the closed rod slot configuration.

To prevent the first rod from becoming displaced from the closed rod slot (e.g., popping out), the jaws of the connector may be configured to interdigitate with each other. As shown, a lateral-extending, outward-facing tooth 1026 may protrude from a proximal tip or end of the fixed jaw portion 1014. The tooth 1026 may be configured to interdigitate with a lateral-extending, inward-facing pocket 1064 formed in a proximal tip or end of the hook of the moveable jaw 1056. The tooth 1026 may have a substantially rectangular or other suitable shape that may be received in the pocket 1064. The tooth 1026 may have a width that is narrower than the width of the moveable jaw 1050. Although the tooth as shown is formed on the fixed jaw, the interdigitating arrangement may be flipped. For example, a tooth may be formed on the movable jaw and a tooth-receiving pocket may be formed in the fixed jaw. While a single tooth and a single pocket are shown, in other arrangements the connector can include a plurality of interdigitating features.

The moveable jaw 1050 may have a reduced width relative to the base portion of the connector body 1012 to minimize the run-on rod length of the jaw along a longitudinal axis of the first rod. For example, the reduced width of the moveable jaw may be less than or equal to 8 millimeters, and preferably less than or equal to 4 millimeters.

Opposing lead-in surfaces 1066a and 1066b (collectively 1066) may be formed in the proximal ends of the moveable jaw 1050 and the fixed jaw portion 1014 to facilitate insertion of the first rod. The lead-in surfaces 1066 may be ramped bearing surfaces oriented obliquely at opposite angles to form a V-shaped lead-in. Other lead-in surface configurations may also be used. As the first rod is pushed against the lead-in surfaces 1066, the moveable jaw 1050 may be urged to translate laterally in a first axial direction away from the connector body 1010, making it easier to open the rod slot between the fixed jaw portion and the moveable jaw.

Figure 11A:
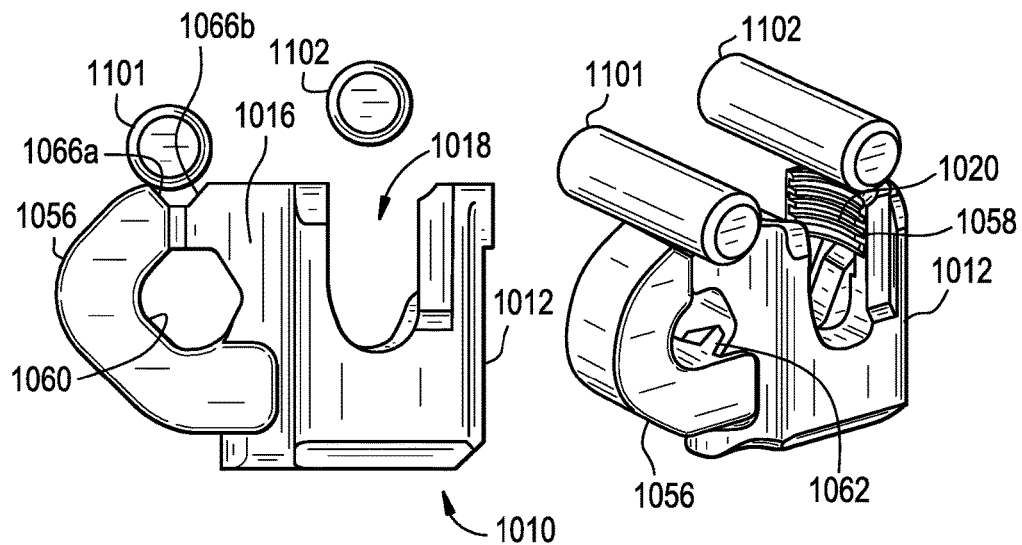
FIGS. 11A through 11D are schematic diagrams illustrating an operation of the rod-to-rod connector according to the fourth embodiment.
Figure 11B:
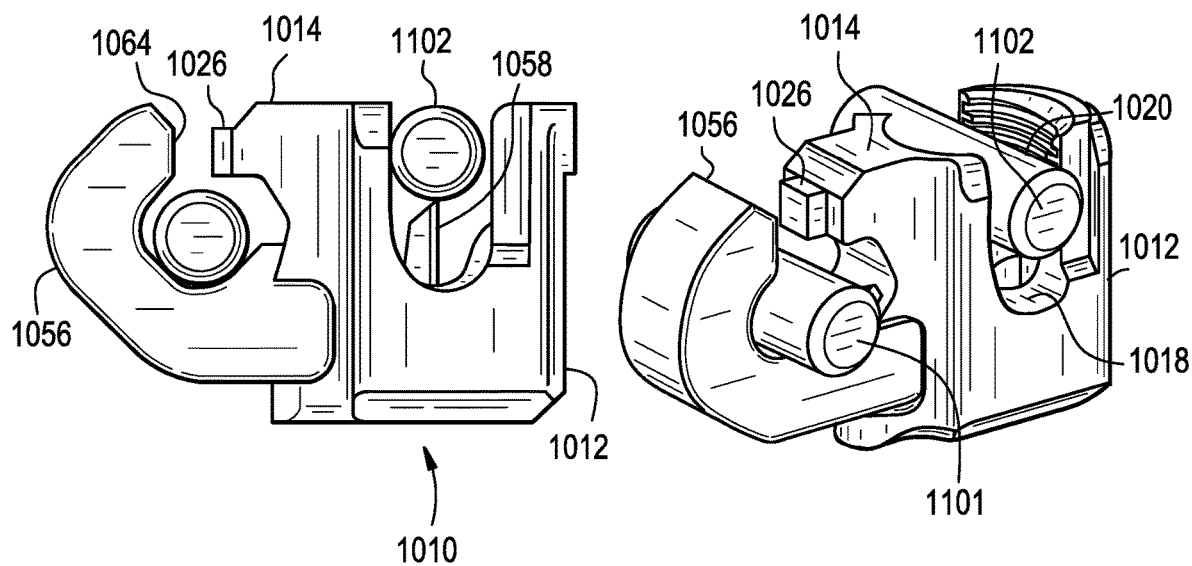
Figure 11C:
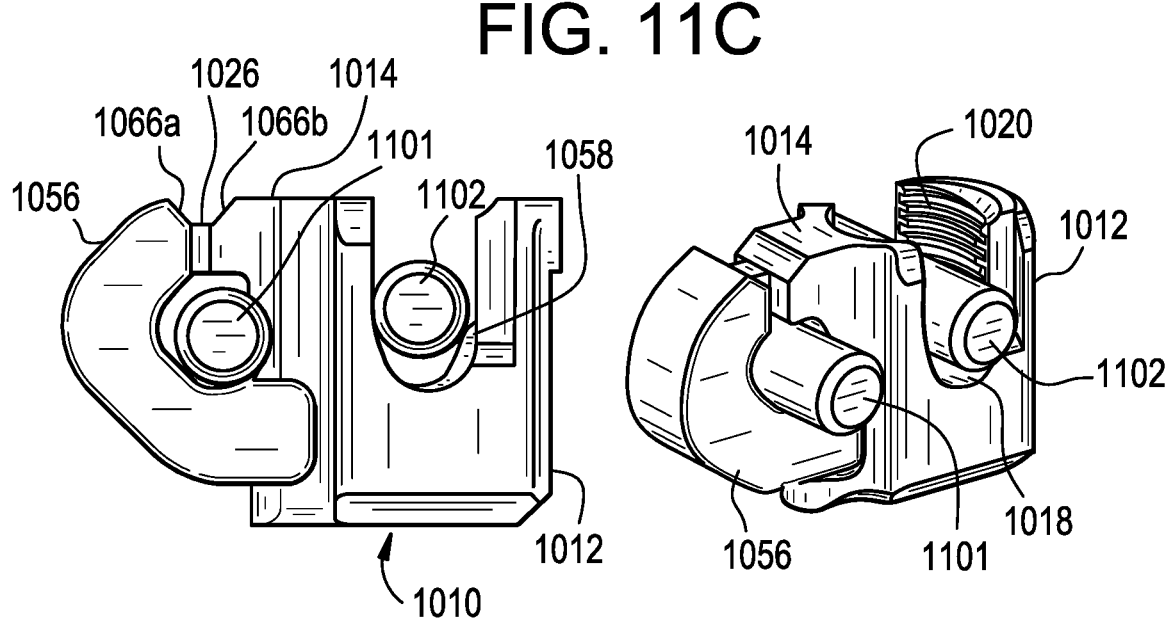
Figure 11D:
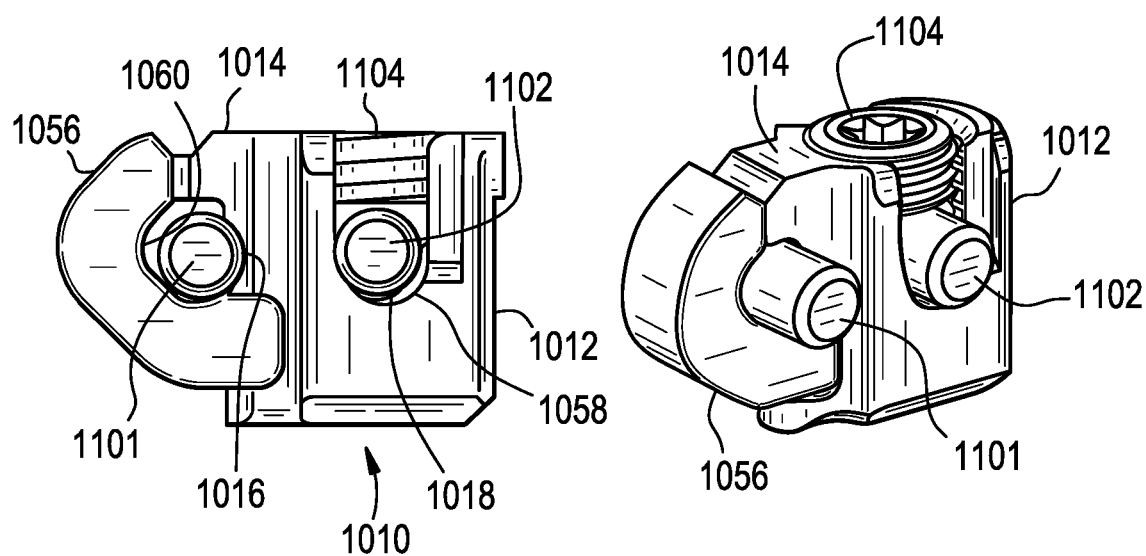

FIGS. 11A through 11D are schematic diagrams illustrating an operation of the rod-to-rod connector 1000 according to the fourth embodiment. As shown in FIG. 11A, the moveable jaw 1050 and the fixed jaw portion 1014 may be initially arranged in a closed rod slot configuration. To insert a first rod 1101 into the connector 1000, the first rod may be pushed against the lead-in surfaces of the jaws 1066, thereby urging the moveable jaw 1050 to slide along the tunnel 1066 in a first axial direction away from the connector body 1010. The first axial direction may be perpendicular to a proximal-distal axis of the second rod-receiving slot 1018. The moveable jaw 1050 may also be urged to slide open by rotating the connector 1000 until the force of gravity pulls the jaw open. As shown in FIG. 11B, with the proximal end of the hook 1056 separated from the fixed jaw portion of the connector body 1014, an open rod slot may be formed between the inward-facing rod-receiving recess of the hook 1060 and the outward-facing recess of the fixed jaw portion 1016 to facilitate insertion of the first rod 1101. The stop tab 1062 formed on the proximal surface of the moveable jaw 1050 may also be used to guide and seat the first rod 1101 in the open slot. In the open rod slot configuration, the axial movement causes the proximal-facing ramped bearing surface 1058 at the back end of the moveable jaw 1054 to enter the second rod-receiving slot 1018. Once the first rod 1101 is inserted into the open rod slot, the second rod 1102 may be inserted into the second rod-receiving slot 1018. As shown in FIG. 11C, the insertion of the second rod 1102 may exert a distal force on the proximal-facing ramped bearing surface 1058 and thereby urge the moveable jaw 1050 to slide in a counter-axial direction through the tunnel of the connector body 1022. As the jaw 1050 slides in the counter-axial direction, the second rod 1102 slides distally until the rod is seated at the base of the slot 1018. The counter-axial movement also causes the tooth 1026 protruding from the fixed jaw portion 1014 to interdigitate or otherwise engage with the tooth-receiving pocket 1064 of the hook 1056, and thereby form a closed rod slot around the first rod 1101 between the inward-facing and outward-facing rod-receiving recesses 1060 and 1016. As shown in FIG. 11D, by tightening the set screw 1104 within the threaded portion of the second rod-receiving slot 1020, the first rod 1101 may be locked within the closed rod slot simultaneously with the second rod 1102 being locked within the second rod-receiving slot 1018. By locking the second rod 1102 in the second rod-receiving slot 1018 with a set screw, a lateral force exerted by the second rod against the proximally-extending ramped bearing surface may continue to provide a mechanical advantage in the clamping force of the moveable jaw against the fixed jaw portion.

Figure 12A:
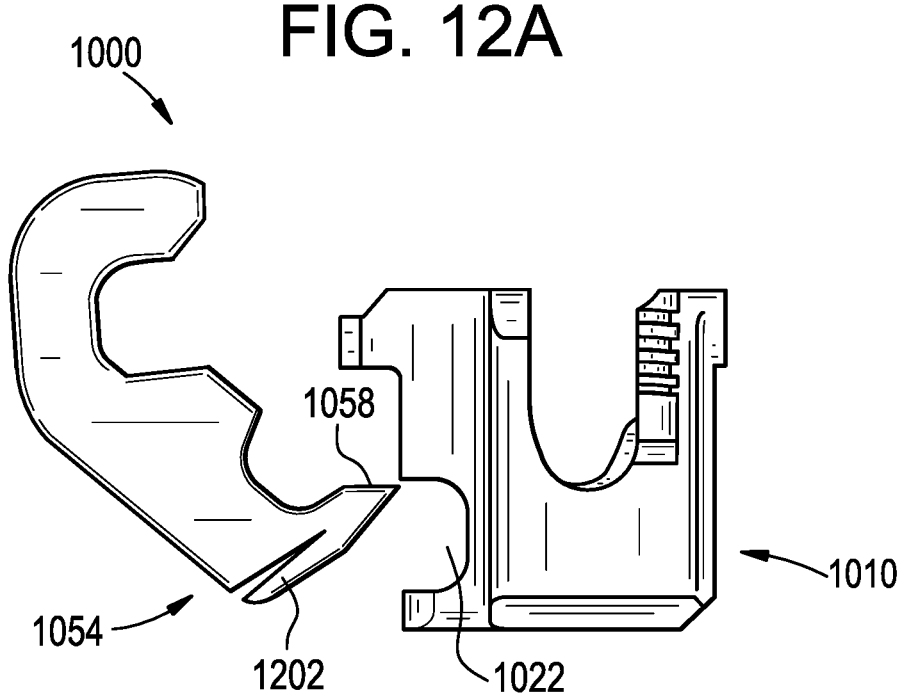
FIGS. 12A and 12B are schematic diagrams that illustrate cross-sectional views of a coupling mechanism between the moveable jaw and the connector body according to the fourth embodiment.
Figure 12B:
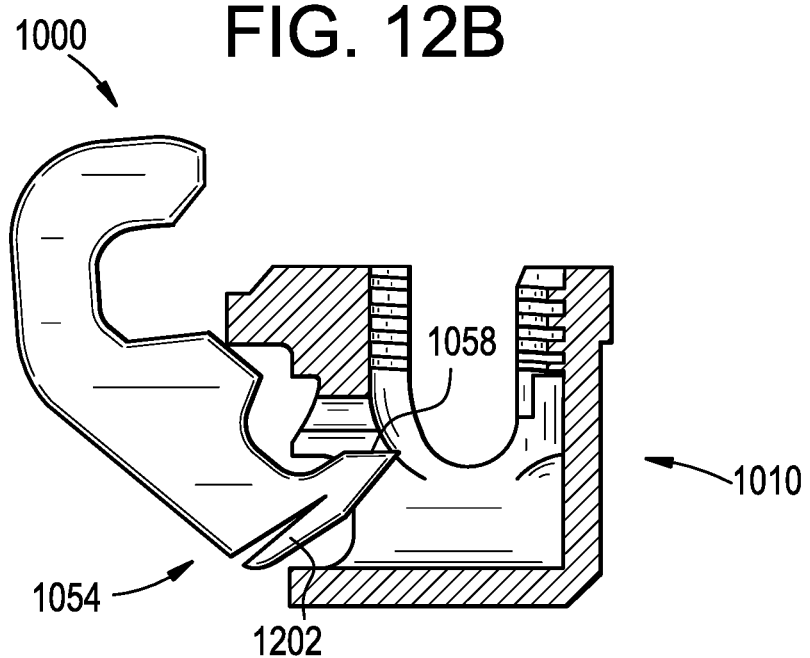

FIGS. 12A and 12B are schematic diagrams that illustrate cross-sectional views of a mechanism for coupling the moveable jaw 1050 and the connector body 1010 of the rod-to-rod connector 1000 according to the fourth embodiment. As shown, a cantilevered end portion 1202 may be formed by a thin wire cut distally adjacent to the ramped bearing surface 1058. The cantilevered end portion 1202 may act as a unidirectional spring that facilitates the coupling of the moveable jaw 1050 with the connector body 1010. As shown in FIGS. 12A and 12B, the moveable jaw 1050 is pivoted into the tunnel of the connector body 1022. As the moveable jaw 1050 enters the tunnel 1022, the cantilevered end portion 1202 deflects inward towards the body of the jaw 1050 until the ramped bearing surface 1058 passes through the tunnel 1022 and into the second rod-receiving slot 1018. Once inserted, the cantilevered end portion 1202 springs outward to prevent the moveable jaw 1050 being decoupled from the connector body 1010. The distal end of the cantilevered end portion 1202 can include a ramped, curved, or tapered contact surface.

Figure 13A:
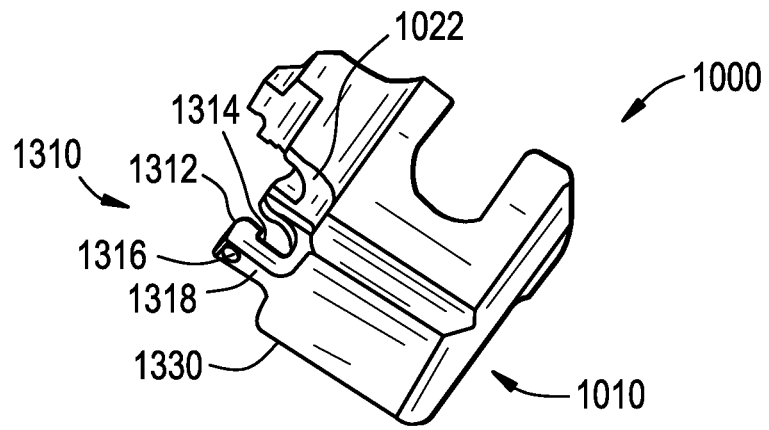
FIGS. 13A, 13B, and 13C are schematic diagrams that illustrate perspective and cross-sectional views of another mechanism for coupling the moveable jaw and the connector body of the rod-to-rod connector according to the fourth embodiment.
Figure 13B:
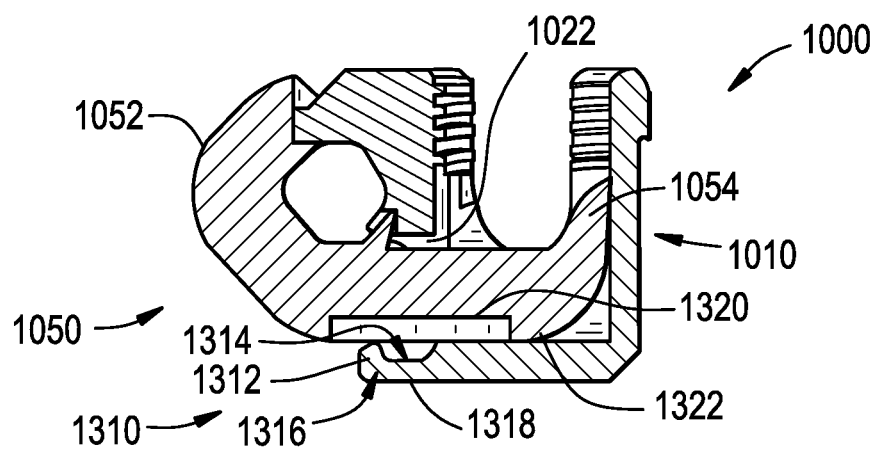
Figure 13C:
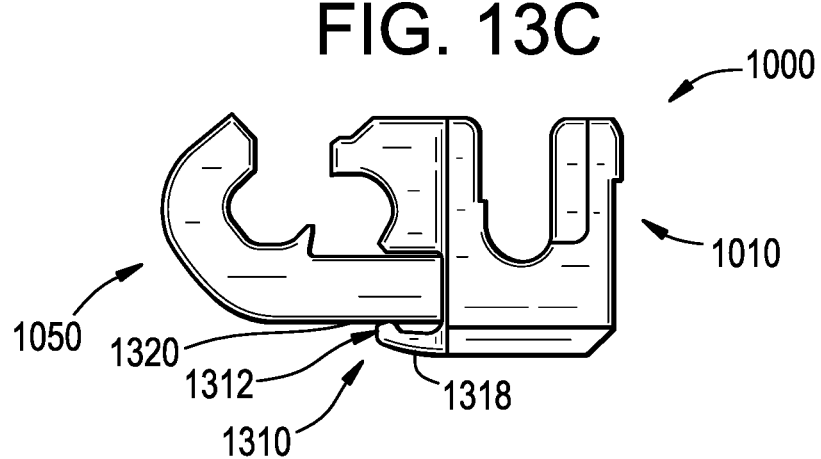

FIGS. 13A, 13B, and 13C are schematic diagrams that illustrate perspective and cross-sectional views of another mechanism for coupling the moveable jaw 1050 and the connector body 1010 of the rod-to-rod connector 1000 according to the fourth embodiment. As shown, the coupling mechanism may include a malleable swaging arm 1310 that may be bent to form a loose coupling with a swage-receiving slot 1320 of the moveable jaw 1050.

FIG. 13A illustrates a swaging arm 1310 of the connector body 1050 according to an embodiment. As shown, the swaging arm 1310 may extend from a distal-facing bottom wall 1330 of the connector body 1010 distally adjacent to the tunnel 1022. The swaging arm 1310 may include a proximal-facing swage 1312 formed at a free end of the swaging arm. The proximal-facing swage 1312 may be a ridge, hook, or other protrusion sized to fit within the swage-receiving slot 1320 of the moveable jaw 1050. The swaging arm 1310 may further include a concave recess 1314 formed in a proximal-facing surface. The concave recess 1314 may be shaped so that the jaw 1050 may be pivoted into the tunnel 1052 of the connector body 1010 during assembly. A dimple 1316 may be formed on a distal-facing surface opposite the proximal-facing swage 1312 to locate a spot on the swaging arm 1310 to apply the bending force by a mallet, press, clamp, or other bending tool. The swaging arm 1310 may include a bend zone 1318 having a reduced thickness to facilitate bending of the swaging arm in that region.

FIG. 13B illustrates the swaging arm 1310 of FIG. 13A prior to coupling to a swage-receiving slot 1320 of the moveable jaw 1050. As shown, the swage-receiving slot 1320 may be formed in a distal-facing bottom wall 1322 of the moveable jaw 1050 between the front end 1052 and the back end 1054. The length of the swage-receiving slot 1320 may be defined to bound the extent of the movement of the jaw 1050 within the tunnel 1022.

FIG. 13C illustrates the swaging arm 1310 of FIG. 13A after coupling to the swage-receiving slot 1320 of FIG. 13B. As shown, the swaging arm 1310 may be bent in a proximal direction to insert the swage 1312 into the swage-receiving slot 1320 of the jaw 1050. The swaging arm 1310 may be bent using a mallet, press, clamp, or other bending tool. During operation, as the moveable jaw slides along the tunnel 1022, the swage-receiving slot 1320 slides over the swage 1312. The jaw 1050 may be prevented from sliding out or otherwise decoupling from the connector body 1010 by the swage 1312 contacting or otherwise abutting a terminal end 1324 of the slot 1320 adjacent to the back end of the jaw 1054.

Although the coupling mechanism of FIGS. 13A-13C are illustrated for use with the rod-to-rod connector 1000 of FIGS. 10A through 11D, the coupling mechanism of FIGS. 13A-13C may be incorporated into any of the rod-to-rod connectors 100, 400, and 700 shown and described with respect to FIGS. 1A-9D.

Figure 14:
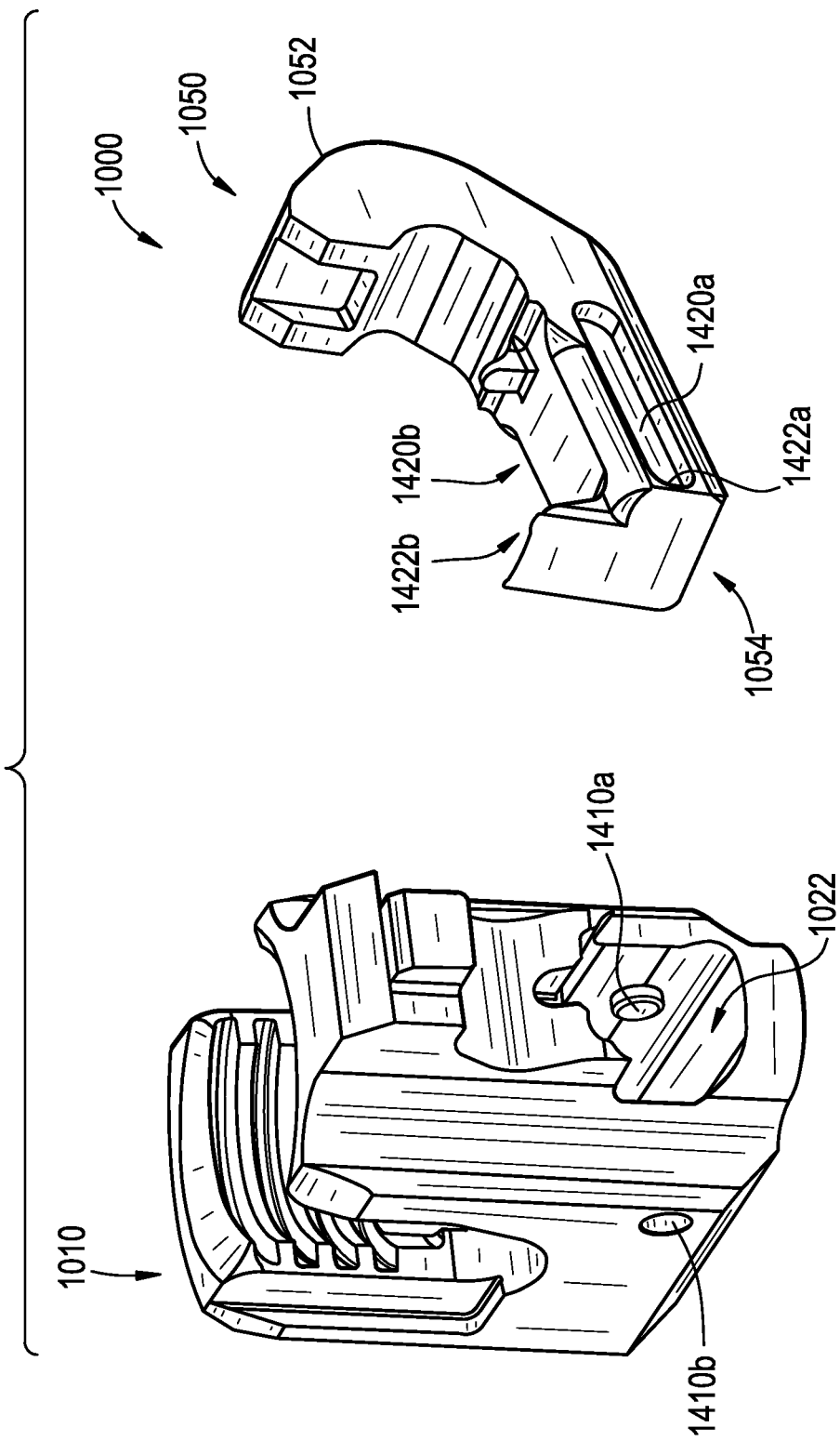
FIG. 14 is a schematic diagram that illustrates a perspective view of another mechanism for coupling the moveable jaw and the connector body of the rod-to-rod connector according to the fourth embodiment.

FIG. 14 is a schematic diagram that illustrates a perspective view of another mechanism for coupling the moveable jaw 1050 and the connector body 1010 of the rod-to-rod connector 1000 according to the fourth embodiment. As shown, the coupling mechanism may include swages 1410*a* and 1410*b* (collectively 1410) formed in opposing sidewalls 1412*a* and 1412*b* (collectively 1412) of the connector body 1050. The swages 1410 may be formed using a punch tool after the moveable jaw 1050 is inserted into the tunnel 1022. The swages 1410 may be protrusions that extend into the tunnel 1022 and are configured to loosely couple the connector body 1010 to swage-receiving slots 1420a and 1420b (collectively 1420) of the moveable jaw 1050. The swage-receiving slots 1420 may be formed in the sidewalls of the moveable jaw 1050. The length of the respective swage-receiving slots 1420 between the front end 1052 and the back end 1054 of the jaw 1050 may be defined to bound the extent of the jaw's movement within the tunnel 1022 of the connector body. During operation, as the moveable jaw 1050 slides along the tunnel 1022, the swage-receiving slots 1420 slide over the respective swages 1410. The jaw 1050 may be prevented from sliding out or otherwise decoupling from the connector body 1010 by the swages 1410 contacting or otherwise abutting the terminal ends 1422a and 1422b (collectively 1422) of the respective slots 1420 adjacent to the back end of the jaw 1054. Although FIG. 14 shows swages 1410 loosely coupled to respective swage-receiving slots 1420 on opposing sides of the jaw 1050, other embodiments may include a swage loosely coupled to a swage-receiving slot on one side of the jaw.

Although the coupling mechanism of FIG. 14 is illustrated for use with the rod-to-rod connector 1000 of FIGS. 10A through 11D, the coupling mechanism of FIG. 14 may be incorporated into any of the rod-to-rod connectors 100, 400, and 700 shown and described with respect to FIGS. 1A-9D.

Other techniques known to one of ordinary skill in the art can be used for coupling or joining the moveable jaw 1050 to the connector body 1010.

The devices disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The preceding description of the disclosed embodiments is provided to enable any person skilled in the art to make or use what is described. Various modifications to these embodiments will be readily apparent to those skilled in the art, and the generic principles defined herein may be applied to other embodiments without departing from the scope of the present disclosure. Thus, the present disclosure is not intended to be limited to the embodiments shown herein but is to be accorded the widest scope consistent with the principles and features disclosed herein.

The invention claimed is:

1. A rod-to-rod connector, comprising:
   a connector body defining first rod-receiving slot and a second rod-receiving recess; and
   a moveable jaw defining a counterpart second rod-receiving recess and moveably coupled to the connector body;
   wherein the movable jaw is configured to move relative to the connector body in response to positioning a first rod in the first rod-receiving slot; and
   wherein the moveable jaw is configured to be locked relative to the connector body in a position that forms at least a substantially closed rod slot around a second rod between the second rod-receiving recess of the connector and the counterpart second rod-receiving recess of the moveable jaw in response to the first rod being locked in the first rod-receiving slot.

2. The rod-to-rod connector of claim 1, wherein the second rod-receiving recess of the connector body is a distal-facing rod-receiving recess formed in a fixed jaw portion extending laterally from a proximal end of the connector body and the counterpart second rod-receiving recess of the moveable jaw is a proximal-facing rod-receiving recess.

3. The rod-to-rod connector of claim 2, wherein the moveable jaw is configured to pivot about a first pivot axis of the connector body.

4. The rod-to-rod connector of claim 3, wherein:
   the moveable jaw is configured to pivot clockwise about the first pivot axis to form an open rod slot for receiving the second rod between the distal-facing rod-receiving recess of the fixed jaw portion of the connector body and the proximal-facing rod-receiving recess of the moveable jaw; and
   the moveable jaw is configured to pivot counter-clockwise about the first pivot axis to form the closed rod slot around the second rod between the distal-facing rod-receiving recess of the fixed jaw portion of the connector body and the proximal-facing rod-receiving recess of the moveable jaw.

5. The rod-to-rod connector of claim 4, further comprising:
   a pivot block having a saddle disposed within a cavity formed in a distal end portion of the connector body and moveably coupled to the connector body and to the moveable jaw, wherein the pivot block is configured to pivot about a second pivot axis of the connector body in response to respective movements of the saddle and the moveable jaw.

6. The rod-to-rod connector of claim 5, wherein the pivot block is configured to pivot counter-clockwise about the second pivot axis and to thereby raise the saddle into the first rod-receiving slot in response to the moveable jaw pivoting clockwise about the first pivot axis to form the open rod slot for receiving the second rod.

7. The rod-to-rod connector of claim 6, wherein the pivot block is configured to pivot clockwise about the second pivot axis and to thereby cause the moveable jaw to pivot counter-clockwise about the first pivot axis to form the closed rod slot around the second rod in response to the first rod exerting a distal force on the saddle of the pivot block.

8. The rod-to-rod connector of claim 7, further comprising a set screw, wherein the second rod is locked within the closed rod slot and the first rod is locked within the first rod-receiving slot in response to tightening the set screw within a threaded portion of the first rod-receiving slot.

9. The rod-to-rod connector of claim 5, wherein the pivot block is moveably coupled to the moveable jaw by a pin-in-slot connection.

10. The rod-to-rod connector of claim 4, wherein the moveable jaw further defines a proximal-facing bearing surface disposed in a cavity formed in the connector body distal to the first rod-receiving slot.

11. The rod-to-rod connector of claim 10, wherein the proximal-facing rod bearing surface is raised into the first rod-receiving slot in response to the moveable jaw pivoting distally to form the open rod slot for receiving the second rod.

12. The rod-to-rod connector of claim 11, wherein the moveable jaw pivots proximally to form the closed rod slot in response to the first rod exerting a distal force in the first rod-receiving slot on the proximal-facing rod bearing surface of the moveable jaw.

13. The rod-to-rod connector of claim 12, further comprising a tooth protruding from an end portion of the moveable jaw and a tooth-receiving pocket formed in a laterally extending jaw of the connector body, wherein the tooth of the moveable jaw is configured to interdigitate with the tooth-receiving pocket of the jaw of the connector body.

14. The rod-to-rod connector of claim 2, wherein the moveable jaw comprises a plurality of proximally extending threaded arms forming a proximal-facing threaded recess there between, wherein the proximal-facing threaded recess is aligned with a proximal-distal axis of the first rod-receiving slot of the connector body.

15. The rod-to-rod connector of claim 14, further comprising a set screw, wherein the moveable jaw is configured to translate within a cavity formed in the connector body along the proximal-distal axis of the first rod-receiving slot in response to tightening the set screw within the proximal-facing threaded recess of the moveable jaw.

16. The rod-to-rod connector of claim 15, wherein the moveable jaw is configured to translate proximally along the proximal-distal axis of the first rod-receiving slot and to thereby form the closed rod slot around the second rod between the distal-facing rod-receiving recess of the fixed jaw portion of the connector body and the proximal-facing rod-receiving recess of the moveable jaw in response to tightening the set screw within the proximal-facing threaded recess.

17. The rod-to-rod connector of claim 16, wherein the second rod is locked within the closed rod slot and the first rod is locked within the first rod-receiving slot in response to tightening the set screw within the proximal-facing threaded recess of the moveable jaw.

18. The rod-to-rod connector of claim 15, wherein the moveable jaw is configured to translate distally along the proximal-distal axis of the first rod-receiving slot and to thereby form an open rod slot between the distal-facing rod-receiving recess of the fixed jaw portion of the connector body and the proximal-facing rod-receiving recess of the moveable jaw.

19. The rod-to-rod connector of claim 15, wherein the moveable jaw is spring-biased to form an open rod slot between the distal-facing rod-receiving recess of the fixed jaw portion of the connector body and the proximal-facing rod-receiving recess of the moveable jaw.

20. The rod-to-rod connector of claim 15, further comprising a tongue protruding along at least one of the plurality of proximally extending threaded arms and configured to offset a torque exerted by the set screw while tightening the set screw within the proximal-facing threaded recess of the moveable jaw.

21. The rod-to-rod connector of claim 14, wherein the moveable jaw is moveably coupled to the connector body by a pin-in-slot connection.

22. The rod-to-rod connector of claim 2, wherein each of the moveable jaw and the fixed jaw portion of the connector body has a run-on width equal to or less than 4 millimeters.

23. The rod-to-rod connector of claim 2, wherein each of the moveable jaw and the fixed jaw portion have a run-on width that is smaller than a width of the connector body.

24. The rod-to-rod connector of claim 1, wherein the second rod-receiving recess is an outward-facing rod-receiving recess formed in a fixed jaw portion extending vertically along a lateral face of the connector body and the counterpart second rod-receiving recess of the moveable jaw is an inward-facing rod-receiving recess that opposes the outward-facing rod-receiving recess of the fixed jaw portion.

25. The rod-to-rod connector of claim 24, wherein the moveable jaw forms a hook at one end that defines the inward-facing rod-receiving recess and a proximal-facing ramped bearing surface protruding at an opposite end.

26. The rod-to-rod connector of claim 25 wherein the moveable jaw is slidably disposed within a tunnel formed in a distal end portion of the connector body between the hook and the ramped bearing surface.

27. The rod-to-rod connector of claim 26, wherein the inward-facing rod-receiving recess of the hook and the outward-facing rod-receiving recess of the fixed jaw portion of the connector body are configured to form an open rod slot for receiving the second rod in response to the moveable jaw sliding in a first axial direction through the tunnel of the connector body.

28. The rod-to-rod connector of claim 27, wherein the proximal-facing ramped bearing surface is configured to enter the first rod-receiving slot of the connector body in response to the moveable jaw sliding in the first axial direction through the tunnel of the connector body.

29. The rod-to-rod connector of claim 28, wherein the moveable jaw is configured to slide in a second axial direction through the tunnel of the connector body and to thereby form the closed rod slot around the second rod between the inward-facing rod-receiving recess of the hook and the outward-facing rod-receiving recess of the fixed jaw portion of the connector body in response to the first rod exerting a distal force on the proximal-facing ramped bearing surface and thereby urging the ramped bearing surface out of the first rod-receiving slot.

30. The rod-to-rod connector of claim 29, further comprising a set screw, wherein the second rod is locked within the closed rod slot and the first rod is locked within the first rod-receiving slot in response to tightening the set screw within the first rod-receiving slot.

31. The rod-to-rod connector of claim 26, wherein the moveable jaw has a cantilevered spring element formed in a distal end of the moveable jaw and configured to deflect towards the distal end of the moveable jaw to facilitate insertion of the moveable jaw into the tunnel of the connector body.

32. The rod-to-rod connector of claim 26, wherein:
the moveable jaw comprises a swage-receiving slot formed in a distal-facing wall of the moveable jaw; and
the connector body comprises a swaging arm having a swage formed at a free end of the swaging arm, wherein the swaging arm extends from a bottom wall of the connector body adjacent to the tunnel and is configured to bend towards the tunnel such that the swage is loosely coupled to the swage-receiving slot.

33. The rod-to-rod connector of claim 26, wherein:
the moveable jaw comprises one or more swage-receiving slots formed in one or more respective sidewalls of the moveable jaw; and
the connector body comprises one or more swages protruding into the tunnel such that the one or more swages are loosely coupled to the one or more swage-receiving slots of the moveable jaw.

34. The rod-to-rod connector of claim 24, wherein each of the moveable jaw and the fixed jaw portion of the connector body has a run-on width equal to or less than 4 millimeters.

35. A method of connecting a first spinal rod and a second spinal rod, comprising:
inserting the first spinal rod in a first rod-receiving slot defined between a first rod-receiving recess formed in a connector body of a connector and a counterpart first rod-receiving recess formed in a moveable jaw of the connector;

moving the moveable jaw, in response to a second rod being positioned in a second rod-receiving slot formed in the connector body, in a position where the first rod-receiving slot is at least substantially closed around an outer circumference of the first rod between the first rod-receiving recess of the connector body and the counterpart rod-receiving recess of the jaw; and locking the moveable jaw in the position where the first rod-receiving slot is at least substantially closed around the outer circumference of the first rod in response to the second rod being locked in the second rod-receiving slot.

36. The method of claim 35, further comprises:
pivoting the moveable jaw clockwise, prior to locking the moveable jaw, about a first pivot axis to form the first rod-receiving slot for receiving the first rod; and
further comprising moving the jaw in response to the second rod being locked in a second rod-receiving slot formed in the connector body comprises pivoting the movable jaw counter-clockwise about the first pivot axis to close the first rod-receiving slot in response to inserting the second rod into the second rod-receiving slot of the connector body.

37. The method of claim 36, wherein pivoting the movable jaw counter-clockwise about the first pivot axis to close the first rod-receiving slot in response to inserting the second rod into the second rod-receiving slot of the connector body comprises:
pivoting a pivot block clockwise about a second pivot axis in response to the second rod applying a distal force against a saddle formed on the pivot block and raised into the second rod-receiving slot, wherein the pivot block is loosely coupled to the moveable jaw; and
pivoting the movable jaw counter-clockwise about the first pivot axis in response to the pivot block pivoting clockwise about the second pivot axis and thereby closing the first rod-receiving slot about the first rod between the first rod-receiving recess and the counterpart rod-receiving recess.

38. The method of claim 37, further comprising:
pivoting the pivot block counter-clockwise about the second pivot axis in response to the movable jaw pivoting clockwise about the first pivot axis to form the first rod-receiving slot and thereby raising the saddle of the pivot block into the second rod-receiving slot.

39. The method of claim 36, further comprising:
raising a back end of the movable jaw into the second rod-receiving slot in response to pivoting the movable jaw clockwise about the first pivot axis to form the first rod-receiving slot for receiving the first rod.

40. The method of claim 39, wherein pivoting the movable jaw counter-clockwise about the first pivot axis to close the first rod-receiving slot in response to inserting the second rod into the second rod-receiving slot of the connector body comprises pivoting the movable jaw counter-clockwise about the first pivot axis to close the first rod-receiving slot in response to the second rod applying a distal force onto the raised back end of the moveable jaw during insertion of the second rod into the second rod-receiving slot.

41. The method of claim 35, further comprising vertically translating the jaw in a proximal direction to form the first rod-receiving slot for receiving the first rod.

42. The method of claim 41, further comprising moving the jaw in response to the second rod being locked in a second rod-receiving slot formed in the connector body, wherein moving the jaw comprises vertically translating the jaw in a proximal direction to close the first rod-receiving slot in response to tightening a set screw within a proximal-facing threaded recess of the moveable jaw, wherein the proximal-facing threaded recess of the moveable jaw is aligned with the second rod-receiving slot of the connector body.

43. The method of claim 35 further comprises:
sliding the moveable jaw in a first axial direction away from the connector body to form the first rod-receiving slot between the first rod-receiving recess of the connector body and the counterpart first rod-receiving recess of the moveable jaw, wherein the first axial direction is perpendicular to a proximal-distal axis of the second rod-receiving slot.

44. The method of claim 35, further comprising moving the jaw in response to the second rod being locked in the second rod-receiving slot, wherein moving the jaw comprises sliding the moveable jaw in a second axial direction toward the connector body in response to the second rod applying a distal force against a proximal-facing ramped bearing surface that protrudes from a back end of the moveable jaw into the second rod-receiving slot.

* * * * *